(12) United States Patent
Ziemek et al.

(10) Patent No.: US 10,828,070 B2
(45) Date of Patent: Nov. 10, 2020

(54) BONE ANCHOR HOUSING LIMITER

(71) Applicant: Zimmer Biomet Spine, Inc., Broomfield, CO (US)

(72) Inventors: Terry Ziemek, Broomfield, CO (US); David W Castleman, Minneapolis, MN (US)

(73) Assignee: Zimmer Biomet Spine, Inc., Westminster, CO (US)

( * ) Notice: Subject to any disclaimer, the term of this patent is extended or adjusted under 35 U.S.C. 154(b) by 402 days.

(21) Appl. No.: 15/663,188

(22) Filed: Jul. 28, 2017

(65) Prior Publication Data
US 2018/0028236 A1 Feb. 1, 2018

Related U.S. Application Data

(60) Provisional application No. 62/368,345, filed on Jul. 29, 2016, provisional application No. 62/482,136, filed on Apr. 5, 2017.

(51) Int. Cl.
*A61B 17/70* (2006.01)
*A61B 17/86* (2006.01)
(Continued)

(52) U.S. Cl.
CPC ...... *A61B 17/7032* (2013.01); *A61B 17/7035* (2013.01); *A61B 17/863* (2013.01); (Continued)

(58) Field of Classification Search
CPC ............ A61B 17/8605; A61B 17/8685; A61B 17/7032
See application file for complete search history.

(56) References Cited

U.S. PATENT DOCUMENTS 4,711,232 A 12/1987 Fischer et al.
7,951,173 B2 5/2011 Hammill, Sr. et al.
(Continued)

FOREIGN PATENT DOCUMENTS

GB 2512063 9/2014
WO 2010111470 9/2010
(Continued)

OTHER PUBLICATIONS

"U.S. Appl. No. 15/663,174, Restriction Requirement dated Aug. 2, 2019", 8 pgs.
(Continued)

*Primary Examiner* — Olivia C Chang
(74) *Attorney, Agent, or Firm* — Schwegman Lundberg & Woessner, P.A.

(57) ABSTRACT

A bone anchor system can comprise a fastener, a rod housing and a first directional component configured for connection to the fastener. The fastener can comprise a shaft having a shaft diameter, an anchoring projection on the shaft, and a head at an end of the shaft. The rod housing can be connected to the head of the fastener. The first directional component can comprise a first body portion having a first outer diameter larger than the shaft diameter, a first bore extending through the first body portion, the first bore sized to receive the shaft diameter, and a first locking component extending from the first body portion configured to engage the rod housing to limit movement of the housing.

11 Claims, 19 Drawing Sheets

(51) Int. Cl.
*A61B 90/00* (2016.01)
*A61B 17/56* (2006.01)

(52) U.S. Cl.
CPC ...... *A61B 17/8605* (2013.01); *A61B 17/8635* (2013.01); *A61B 17/8685* (2013.01); *A61B 17/8695* (2013.01); *A61B 17/7037* (2013.01); *A61B 2017/564* (2013.01); *A61B 2017/867* (2013.01); *A61B 2017/8655* (2013.01); *A61B 2090/061* (2016.02)

(56) References Cited

U.S. PATENT DOCUMENTS

| | | |
|---|---|---|
| 8,162,998 B2 | 4/2012 | Schlienger et al. |
| 8,163,031 B2 | 4/2012 | Truckai et al. |
| 8,221,479 B2 | 7/2012 | Glazer et al. |
| 8,343,200 B2 | 1/2013 | Khanna et al. |
| 8,496,685 B2 | 7/2013 | Landry et al. |
| 8,512,382 B2 | 8/2013 | Cawley et al. |
| 8,961,568 B2 | 2/2015 | McKinley et al. |
| 9,161,794 B2 | 10/2015 | Garvey |
| 9,216,043 B2 | 12/2015 | Stad et al. |
| 9,289,244 B2 | 3/2016 | Hestad et al. |
| 2005/0273101 A1 | 12/2005 | Schumacher |
| 2006/0217717 A1 | 9/2006 | Whipple |
| 2008/0086131 A1 | 4/2008 | Daly et al. |
| 2010/0057135 A1 | 3/2010 | Heiges et al. |
| 2010/0137920 A1 | 6/2010 | Hammill, Sr. et al. |
| 2011/0106172 A1 | 5/2011 | Wallenstein et al. |
| 2012/0029566 A1* | 2/2012 | Rezach ............ A61B 17/7038 606/264 |
| 2012/0143262 A1 | 6/2012 | Jensen et al. |
| 2013/0018427 A1 | 1/2013 | Pham et al. |
| 2015/0100096 A1* | 4/2015 | Protopsaltis ....... A61B 17/7035 606/306 |
| 2016/0143667 A1 | 5/2016 | Beger et al. |
| 2016/0287301 A1 | 10/2016 | Mehl et al. |
| 2018/0028246 A1 | 2/2018 | Kang et al. |
| 2018/0153588 A1* | 6/2018 | Mosnier ............ A61B 17/7035 |

FOREIGN PATENT DOCUMENTS

| | | |
|---|---|---|
| WO | 2011056707 | 5/2011 |
| WO | WO-2017035186 A1 | 3/2017 |

OTHER PUBLICATIONS

"International Application Serial No. PCT/US2017/044435, International Search Report dated Oct. 30, 2017", 4 pgs.

"International Application Serial No. PCT/US2017/044435, Written Opinion dated Oct. 30, 2017", 7 pgs.

"International Application Serial No. PCT/US2017/044440, International Search Report dated Oct. 30, 2017", 4 pgs.

"International Application Serial No. PCT/US2017/044440, Written Opinion dated Oct. 30, 2017", 6 pgs.

"U.S. Appl. No. 15/663,174, Non Final Office Action dated Oct. 16, 2019", 6 pgs.

"U.S. Appl. No. 15/663,174, Response filed Oct. 2, 2019 to Restriction Requirement dated Aug. 2, 2019", 8 pgs.

"European Application Serial No. 17749087.7, Response to Communication pursuant to Rules 161(1) and 162 EPC filed Sep. 20, 2019", 26 pgs.

"European Application Serial No. 17749326.9, Communication Pursuant to Article 94(3) EPC dated Nov. 22, 2019", 5 pgs.

"European Application Serial No. 17749326.9, Response to Communication pursuant to Rules 161(1) and 162 EPC filed Sep. 23, 2019", 18 pgs.

"U.S. Appl. No. 15/663,174, Final Office Action dated Mar. 20, 2020", 8 pages.

"European Application Serial No. 17749326.9, Response filed Apr. 2, 2020 to Communication Pursuant to Article 94(3) EPC dated Nov. 22, 2019", 13 pages.

* cited by examiner

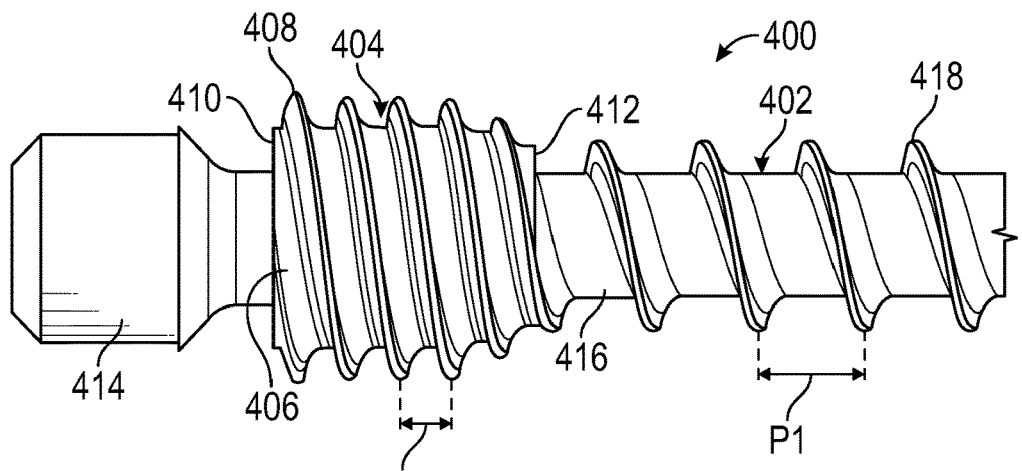
FIG. 13
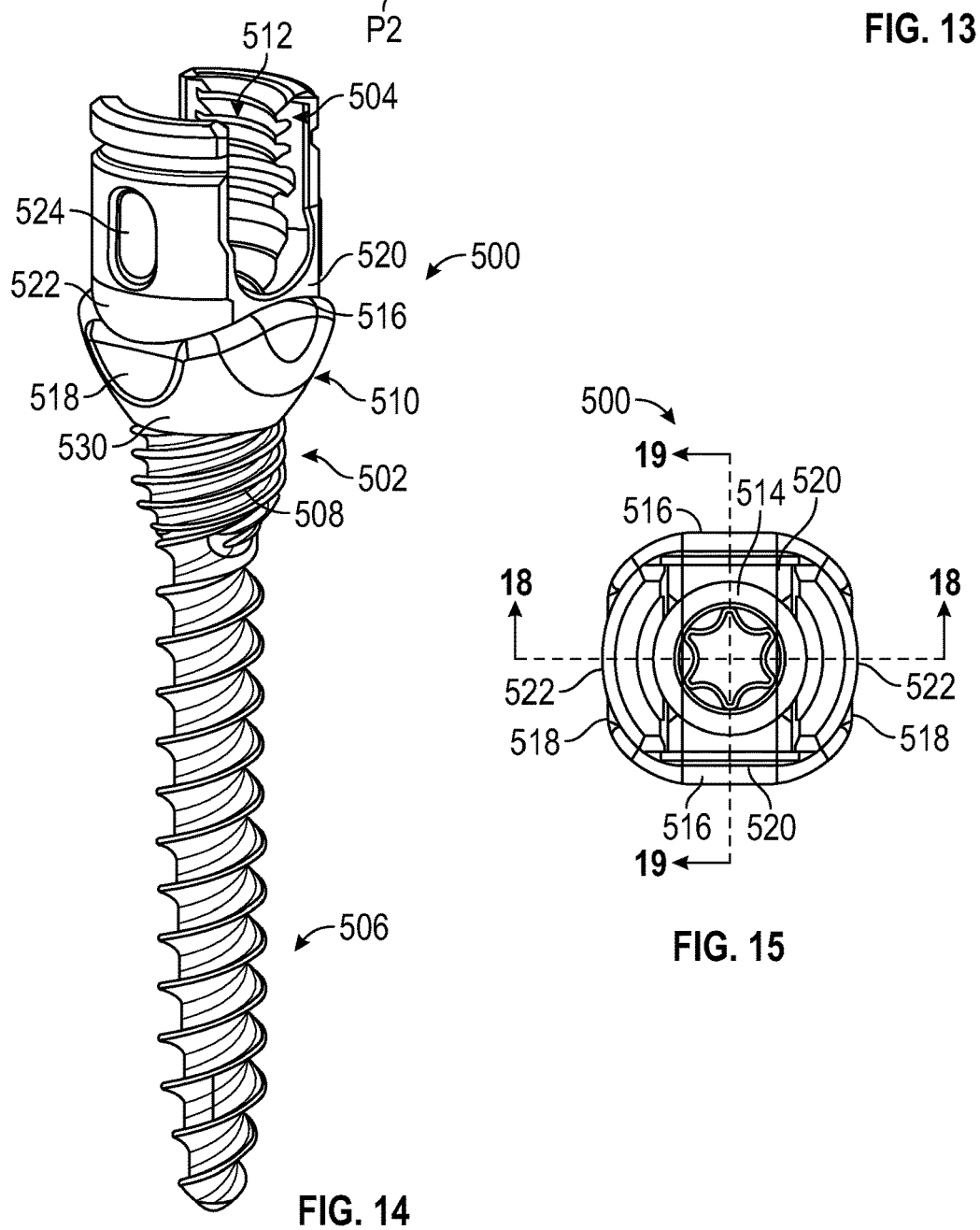
FIG. 14
FIG. 15

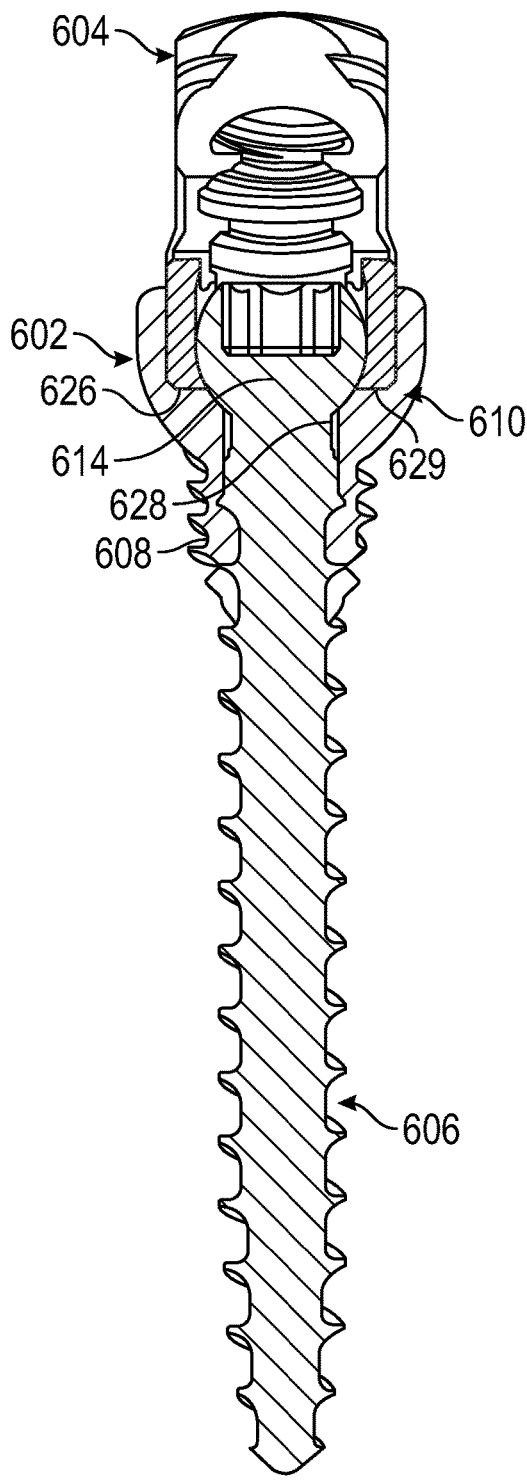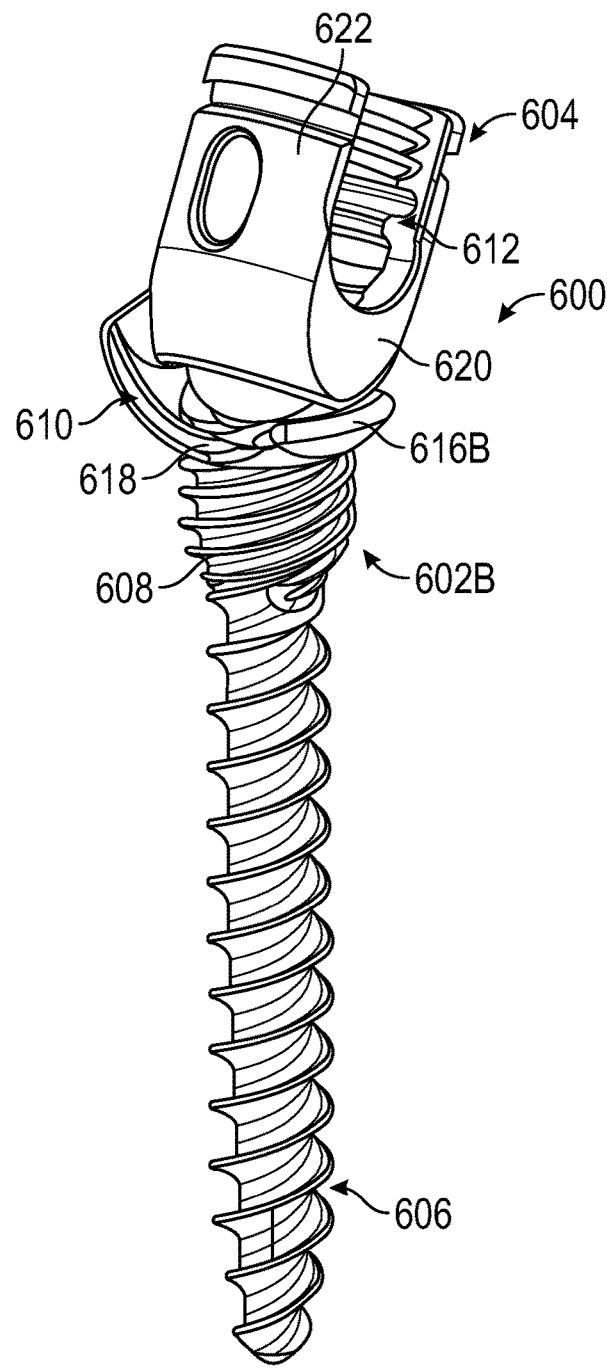
FIG. 31
FIG. 32

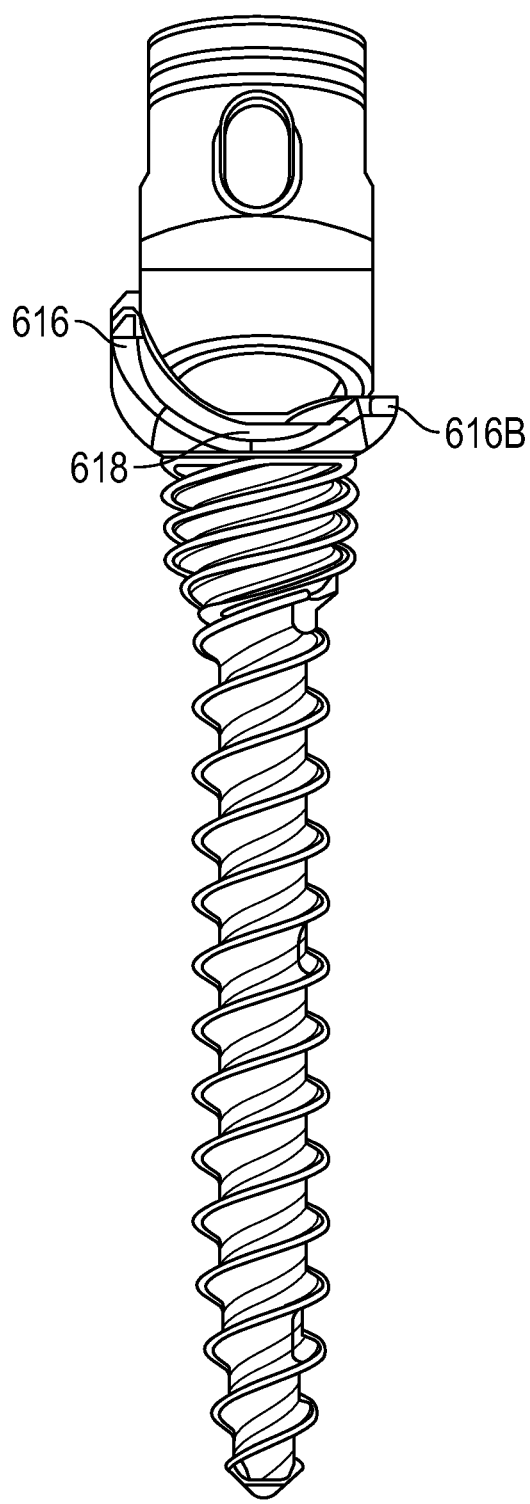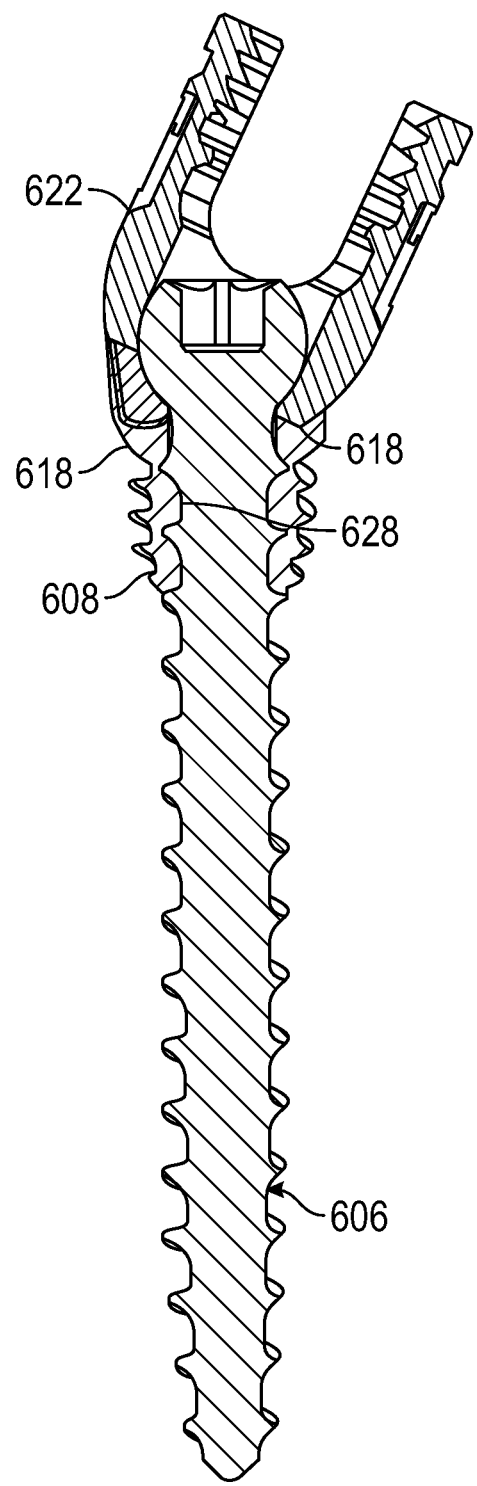
FIG. 35  FIG. 36

BONE ANCHOR HOUSING LIMITER

CLAIM OF PRIORITY

This application claims the benefit of U.S. Provisional Patent Application Ser. No. 62/368,345, filed on Jul. 29, 2016, and claims the benefit of U.S. Provisional Patent Application Ser. No. 62/482,136, filed on Apr. 5, 2017, the benefit of priority of each of which is claimed hereby, and each of which are incorporated by reference herein in its entirety.

TECHNICAL FIELD

This document pertains generally, but not by way of limitation, to systems and methods for fixation of bones during orthopedic procedures. More particularly, this disclosure relates to, but not by way of limitation, vertebral bone anchors particularly suited for use in weakened or degenerative bone.

BACKGROUND

The spinal column of a patient includes a plurality of vertebrae linked to one another by facet joints and an intervertebral disc located between adjacent vertebrae. The facet joints and intervertebral disc allow one vertebra to move relative to an adjacent vertebra, providing the spinal column a range of motion. Diseased, degenerated, damaged, or otherwise impaired facet joints and/or intervertebral discs may cause the patient to experience pain or discomfort and/or loss of motion, thus prompting surgery to alleviate the pain and/or restore motion of the spinal column.

One possible method of treating these conditions is to immobilize a portion of the spine to allow treatment. Traditionally, immobilization has been accomplished by rigid stabilization. For example, in a conventional spinal fusion procedure, a surgeon restores the alignment of the spine or the disc space between vertebrae by installing a rigid fixation rod between pedicle screws secured to adjacent vertebrae. Bone graft is placed between the vertebrae, and the fixation rod cooperates with the screws to immobilize the two vertebrae relative to each other so that the bone graft may fuse with the vertebrae.

Dynamic stabilization has also been used in spinal treatment procedures. Dynamic stabilization does not result in complete immobilization, but instead permits a degree of mobility of the spine while also providing sufficient support and stabilization to effect treatment. Dynamic stabilization systems can include a flexible construct extending between pedicle screws installed in adjacent vertebrae of the spine.

Examples of stabilization systems are the Dynesys® System, the Sequoia® Thoracolumbar Pedicle Screw System and the Lineum® OCT Spine System available from Zimmer Biomet Spine, Inc. of Broomfield, Colo.

OVERVIEW

The present inventors have recognized, among other things, that a problem to be solved can include the need to provide bone anchors, such as threaded fasteners or screws, in bone that is degenerative or otherwise weakened. If bone anchors are inserted into weakened bone, there can be the potential for the fastener to move position or become dislodged, thereby rendering the anchoring effects provided by the fastener less effective or altogether ineffective.

The present subject matter can help provide a solution to various problems associated with the anchoring of fasteners in weakened or partially weakened bone by providing a sizing component that can be coupled to the fastener to enlarge the anchoring footprint of the fastener. The sizing component can be modular such that it can be attached to standard fasteners already typically maintained in inventory and/or can be combined with other sizing components to change the capabilities of the sizing component. Additionally, various sizing components can come in different shapes and configurations to accommodate bone that is weakened or degenerative in different capacities, thereby allowing a practitioner or surgeon the ability to choose from a variety of sizing components for use with particular bone defects of a particular patient. In various examples, the sizing component can be a sleeve into which a fastener is threaded to enlarge all or part of the shaft diameter of the fastener to provide radial anchoring in cancellous bone inside the bone, or a cap into which a fastener is threaded to provide axial anchoring into cortical bone at a surface of the bone.

In an example, the present subject matter can help provide a solution to this problem, such as by providing a bone anchor system that can comprise: a fastener, a rod housing and a first directional component. The fastener can comprise: a shaft having a shaft diameter; an anchoring projection, such as threading, on the shaft; and a head at an end of the shaft. The rod housing can be connected to the head of the fastener. The first directional component can be configured for connection to the fastener. The first directional component can comprise: a first body portion having a first outer diameter larger than the shaft diameter; a first bore extending through the first body portion, the first bore sized to receive the shaft diameter; and a first locking component extending from the first body portion configured to engage the rod housing to limit movement of the housing.

In another example, a bone anchor directional component can comprise a first body portion, a first bore and a first locking component. The first body portion can have a first outer diameter larger than the shaft diameter. The first bore can extend through the first body portion and can be sized to receive a shaft of a bone anchor. The first locking component can extend from the first body portion and can be configured to engage a rod housing of the bone anchor to limit movement of the housing relative to a fastener shaft.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

FIG. 13 is a side view of another exemplary bone anchor including a fastener having a first external thread pitch and a sizing component having a second external thread pitch.

FIG. 14 is a perspective view of a poly-axial bone anchor having a threaded sleeve configured to pivotably and rotationally lock a housing relative to a fastener.

FIG. 15 is a top view of the poly-axial bone anchor of FIG. 14 showing a cup of the threaded sleeve engaging the housing.

FIG. 31 is a cross-sectional view of the poly-axial bone anchor of FIG. 27 taken at section 31-31 showing the high-side of the saddle engaging a flat portion of the housing.

FIG. 32 is a perspective view of a poly-axial bone anchor having a threaded sleeve configured to uni-directionally lock a housing relative to a fastener.

FIG. 35 is a side view of the poly-axial bone anchor of FIG. 32 showing a high-side of the saddle engaging a distractor side of the housing.

FIG. 36 is a cross-sectional view of the poly-axial bone anchor of FIG. 33 taken at section 36-36 showing the low-side of the saddle disengaging the housing.

DETAILED DESCRIPTION

Figures 1, 2:
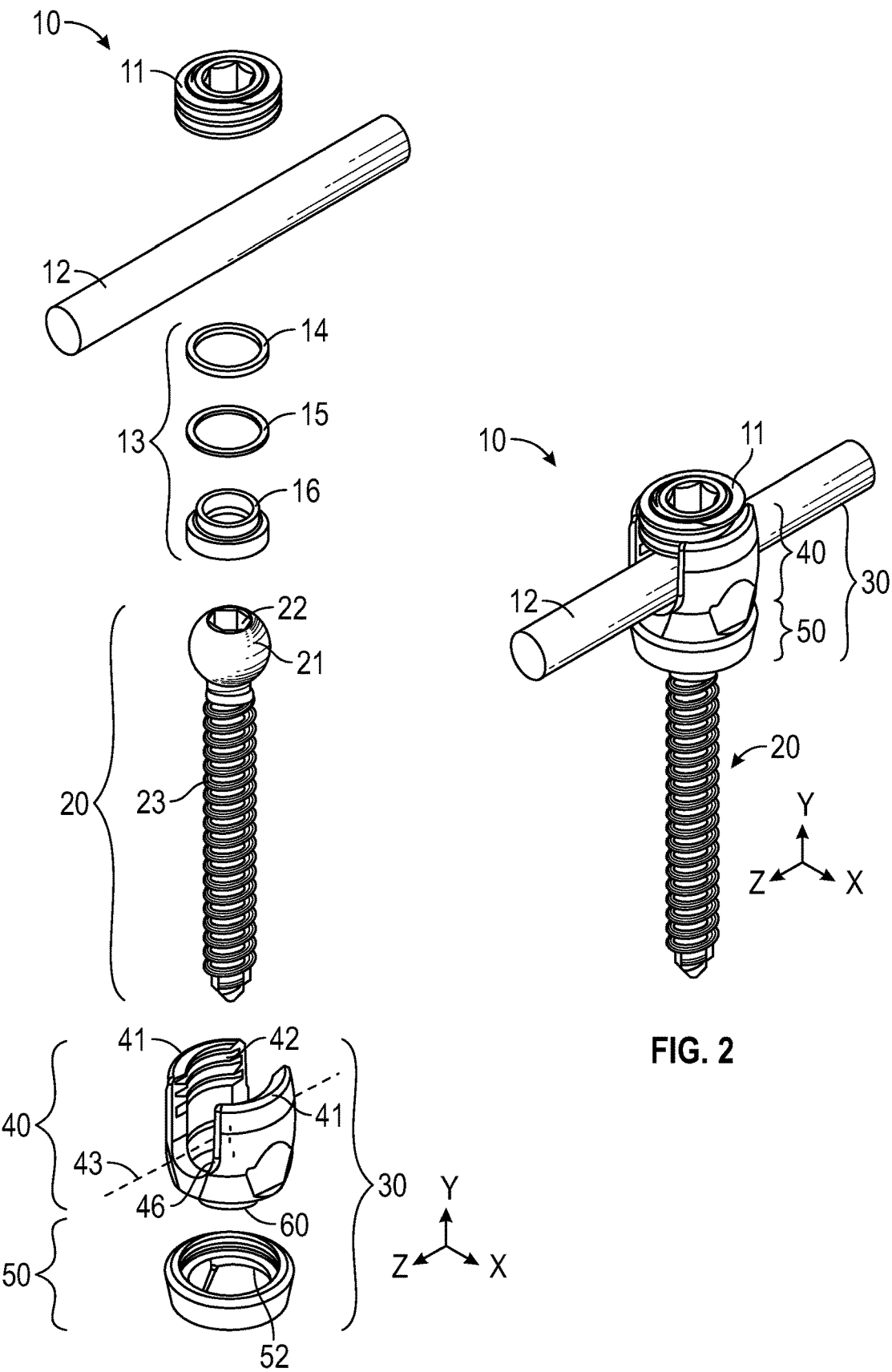
FIG. 1 is an exploded view of an exemplary bone anchor comprising a fastener, a housing, a rod and a closure member.
FIG. 2 is a perspective view of the bone anchor of FIG. 1 showing the rod secured to the housing between the fastener and the closure member.

FIG. 1 is an exploded view illustrating components of exemplary bone anchor 10 and rod 12. Bone anchor 10 can include closure member 11, retainer assembly 13, fastener 20 and housing 30. Retainer assembly 13 can include retainer ring 14, wave washer 15 and seat 16. Fastener 20 can include head 21, keyed portion 22 and shank 23. Housing 30 can include upper housing 40 and lower housing 50. Upper housing 40 can include opposing arms 41, threading 42 and U-shaped channel 43, which extends along a transverse axis that is transverse to the axial axis of fastener shank 23.

FIG. 2 is a perspective view of bone anchor 10 of FIG. 1 showing rod 12 secured to housing 30 between fastener 20 and closure member 11. FIGS. 1 and 2 are discussed concurrently.

Bone anchor 10 can be used to couple rod 12 or another elongate member to a boney structure. For example, shank 23 of fastener 20 can be inserted into and through upper housing 40 and lower housing 50 to connect to a pedicle of a vertebra. Retainer assembly 13 can be inserted into channel 43 to sit below rod 12. Retainer ring 14 can be connected to upper housing 40 to lock wave washer 15 and seat 16 in housing 30 below threading 42, thereby at least partially immobilizing fastener 20 within housing 30. Rod 12 can fit into U-shaped channel 43 formed by opposing arms 41, such as by being inserted into channel 43 from the top or proximal end of housing 30. Closure member 11, which can comprise a set screw or the like, can be threaded into threading 42 to push rod 12 down into channel 43 atop retainer assembly 13, thereby at least partially immobilizing rod 12 within bone anchor 10.

Bone anchor 10 can include particular degrees of adjustability that can help ensure that fastener 20 and elongate member 12 can be locked down at the particular locations and orientations desired by the practitioner or surgeon. For example, head 21 can be spherical in shape to allow rotation within housing 30. In particular, bone anchor 10 can allow for angular deviation of bone screw 20 away from the axial orientation shown in FIG. 1. Such an angular deviation may be referred to as "angulation", and desired angulations may exceed 35 degrees, 40 degrees, 45 degrees, or more, in some instances. Further description of such angulation is described in U.S. Pat. No. 9,289,244 to Hestad et al., which is hereby incorporated herein by this reference in its entirety.

Bone anchor 10 can be delivered or provided to or obtained by a practitioner in a semi-assembled state. In the exemplary design of FIG. 1, housing 30 can be modular, thus formed of multiple components coupled together. For example, housing 30 can include two components that are longitudinally adjacent to each other, namely upper housing 40 and lower housing 50. Thus, upper housing 40 and lower housing 50 can be pre-assembled. Also, fastener 20 can be pre-inserted into housing 30. Housing 30 can have a bore that extends longitudinally through the upper housing 40 and lower housing 50, generally coaxial with the longitudinal axis of bone anchor 10. Upper housing can include bore 46 and lower housing 50 can include bore 52 which can each be aligned and centered along the central axial axis of fastener 20 when fastener 20 is assembled with housing 30.

Fastener 20 can have threaded shank 23 that extends out from the bottom of lower housing 50 at bore 52 after passing through bore 46. Head 21 can be sized such that head 21 can pass into bore 46, but cannot pass through bore 52. Head 21 of fastener 20 can be generally spherical in shape, so that it may pivot with respect to housing 30 on lower housing 50.

Prior to final assembly, shank 23 can be dropped downward or otherwise inserted into the top of housing 30 through upper housing 40 and lower housing 50 so that head 21 can rest on lower housing 50. Alternatively, fastener 20 can be bottom-loaded into upper housing 40, and then lower housing 50 can be positioned around shank 23 and coupled onto upper housing 40, so that head 21 can be held in place within upper housing 40 atop lower housing 50.

Head 21 of fastener 20 can be held in place by retainer assembly 13, which can prevent fastener 20 from being pulled upward out of or otherwise displaced from housing 30. Retainer assembly 13 can allow pivoting of screw head 21 with respect to housing 30. Retainer assembly 13 can be typically in the form of one or more rings having a central aperture, which can allow the practitioner to insert a screwdriver through the apertures of the rings to engage a driver interface such as a keyed portion 22 on head 21 of fastener 20. The exemplary retainer assembly 13 in FIG. 1 can include seat 16 that can contact head 21, biasing member or wave washer 15, and retainer ring 14 farthest away from screw head 21. Seat 16 can include a concave annular region that has a radius of curvature matched to that of screw head 21, which facilitates pivoting of head 21. The concave annular region can also increase the frictional contact with head 21, which facilitates fastener 20 being held in place by seat 16 in the desired angular orientation.

Biasing member 15 can be inserted into channel 43 so as to be disposed on top of seat 16. Retainer ring 14 can be coupled to housing 30, such as via split-ring configuration, to secure biasing member 15 between seat 16 and retainer ring 14. In an example, biasing member 15 and retainer ring 14 can fit around an annular portion of seat 16. Next, rod 12 can be positioned on top of retainer ring 14.

To lock the components of bone anchor 10 in place, the practitioner can screw closure member 11 into threads 42 at the upper portion of housing 30 until closure member 11 engages rod 12. Closure member 11 can force rod 12 against the upper surface of seat 16, pushing retainer ring 14 and biasing member 15 down around seat 16, and in turn can force seat 16 against head 21 of the screw 20. Prior to final tightening of closure member 11, biasing member 15 can cause seat 16 to frictionally engage head 21 to resist movement of housing 30 with respect to fastener 20, which can allow for repositioning of shank 23. After complete tightening of closure member 11, the frictional force between seat 16 of retainer assembly 13 and head 21 can be sufficient to lock fastener 20 in place with respect to housing 30. In an example, U-shaped channel 43 can be deep enough so that closure member 11 does not force rod 12 against the bottom of U-shaped channel 43, with rod 12 being immobilized between seat 16 and closure member 11. In an example, retainer assembly 13 can be omitted, and closure member 11 can force rod 12 directly against head 21 of fastener 20 to secure fastener 20 in place. In an example, closure member 11 can push rod against portions of arms 41 forming the bottom of channel 43 to immobilize rod 12, with or without retainer assembly 14. In such an example with retainer assembly 14, angulation of fastener 20 can be partially immobilized by biasing member 15, and in such an example without retainer assembly 14 fastener 20 can be freely angulated (e.g. is not immobilized).

In practice, fastener 20 is threaded into bone that is structurally sound such that bone anchor 10 is substantially immobilized via engagement of threading on shank 23 extending radially from shank 23 into cancellous bone. However, sometimes bone at a location where it is desirable to provide anchoring by bone anchor 10 is inadequate for immobilizing a fastener. Such inadequate bone can arise from a variety of conditions, such as osteoporosis or other degenerative conditions that cause the bone structure to become compromised and weakened. Sometimes it is impractical to move bone anchor 10 to another location for a variety of reasons, such as there being no other available bone structure to provide anchoring or because a bore has already been drilled into the bone and it would unnecessarily further weaken the bone to drill another hole. The present disclosure addresses these issues in anchoring fasteners in boney structure by providing a sizing component that can be coupled to the fastener to increase the anchoring capacity or footprint of the fastener to reach a larger area and thereby reach healthy or otherwise structurally sound bone for anchoring.

Figure 3:
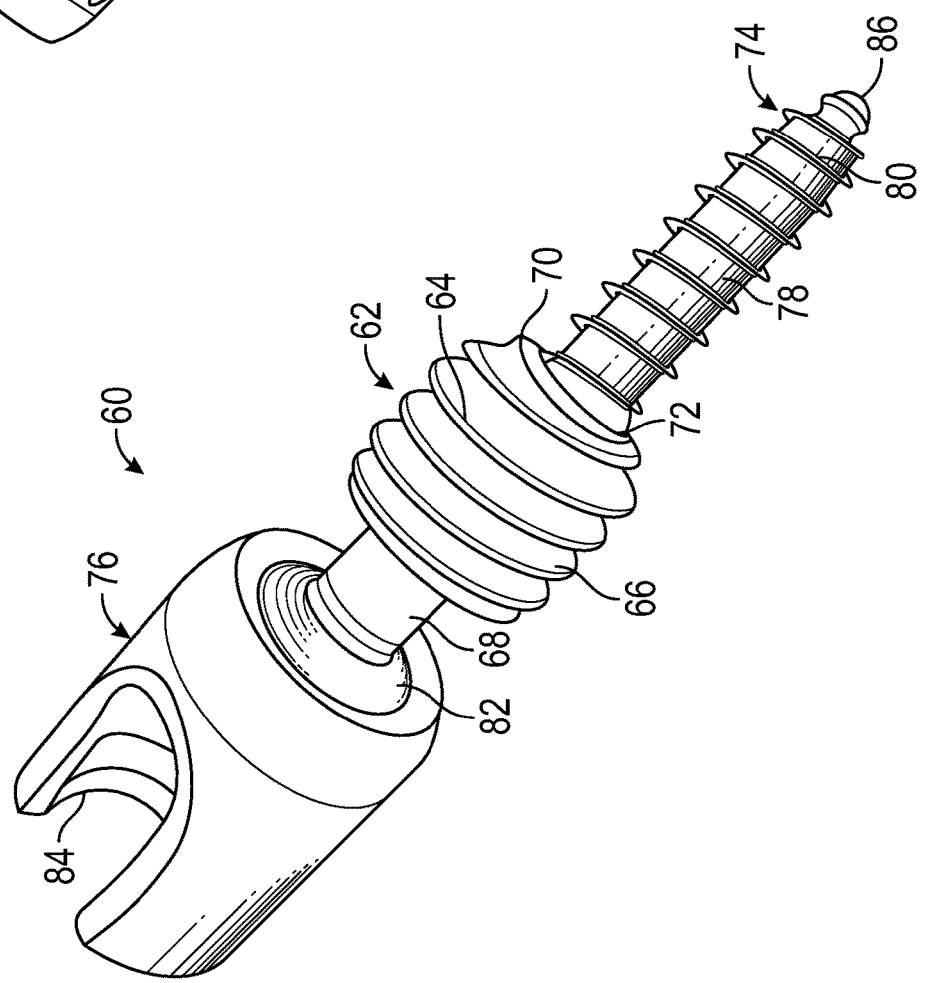
FIG. 3 is a perspective view of an exemplary bone anchor having a first embodiment of a sizing component comprising a threaded sleeve disposed along a shaft of a threaded fastener and having radial extending enlarging threading.

FIG. 3 is a perspective view of exemplary bone anchor 60 having sizing component 62, which can comprise threaded sleeve 64, enlarging threading 66, first end 68, second end 70 and central bore 72. Bone anchor 60 can comprise fastener 74 and housing 76. Fastener 74 can include shaft 78, which can include anchor threading 80.

Bone anchor 60 can function similarly to that of bone anchor 10 of FIG. 1. For example, fastener 74 can include spherical head 82 that can rotate within housing 76, which can include slot 84 for receiving a rod. Sizing component 62 can be sized to mate with shaft 78 of fastener 74. For example, the outer diameter of shaft 78 can be sized to fit within the diameter of central bore 72, and internal female threading ("sizing threading") within central bore 72 can be sized to mate with male anchor threading 80. Sizing component 62, however, can be configured to operate with other bone anchor devices, such as bone anchor 200 of FIGS. 7-9.

Sleeve 64 can extend along a central axis that is configured to be co-axial with the central axis of shaft 78. Sleeve 64 can be tapered between first end 68 and second end 70 in order to provide a smooth transition between the outer diameter of shaft 78 and the outer diameter of sleeve 64. First end 68 of sleeve 64 can have a diameter of the desired outer diameter of sizing component 62. The diameter of first end 68 can be selected to increase the diameter of shaft 78 by any desirable amount to provide a larger anchoring footprint, as discussed below. Second end 70 can have a diameter that is just slightly larger than the outer diameter of shaft 78 sufficient to allow insertion of shaft 78 into sleeve 64. Thus, the diameter of sleeve 64 can increase from second end 70 to first end 68 so that, as shaft 78 is threaded into bone, sizing component 62 can be eased or gradually inserted into the bore in the bone. However, the diameter of sleeve 64 need not increase in a steady manner such that the widest portion of sleeve 64 need not be located at first end 68. Enlarging threading 66 on sleeve 64 can be sized to be the same as anchor threading 80 on shaft 78. For example, threading 66 on sleeve 64 can have the same pitch as threading 80 on shaft 78 to facilitate smooth entry of fastener 74 into a bone bore, particularly one that is pre-tapped with threading. In other words, anchor threading 80 and enlarging threading 66 can have the same pitch, but with different diameters, to ensure fastener 74 and sizing component 62 advance into the bone at the same rate and prevent binding. As such, threading 66 can comprise a continuation of threading 80 that in aggregate extends from tip 86, along shaft 78, onto second end 70, increasing in size along sleeve 64 and to first end 68. In other examples, threading 66 can be dual lead and threading 80 can be single lead with double pitch and have larger valleys to provide deep anchoring in the bone structure, as is discussed in greater detail with reference to FIG. 13.

Sizing component 62 can comprises sleeve 64 that can enlarge the diameter of shaft 78. Thus, as sleeve 64 is threaded onto shaft 78, the outer diameter of sleeve 64 and threading 66 can radially increase the diameter of bone anchor 60 to allow shaft 78 to increase or enlarge the anchoring footprint of fastener 74. In particular, shaft 78 can be configured to anchor bone anchor 60 into a bone bore having approximately the same diameter as shaft 78. However, as discussed, the boney structure may be weakened or deficient such that threads 80 cannot take adequate hold in the boney structure, thereby leaving open the possibility of bone anchor 60 becoming dislodged or displaced. Sleeve 64 can enlarge shaft 78 such that bone anchor 60 can become engaged in bone outside of, or larger than, the diameter of shaft 78. For example, sleeve 64 can be selected to have an outer diameter that is larger than a diseased or weakened bone area surrounding a bone bore into which shaft 78 is threaded. Thus, threading 66 of sleeve 64 can provide anchoring in healthy or structurally sound bone material.

Sleeve 64 can be threaded onto shaft 78 up to the proximal end of threading 80 near spherical head 82. As such, sleeve 64 can be configured to overcome deficient boney structure proximate a cortical bone surface surrounding the bone bore. Additionally, sleeve 64 can provide strengthening of shaft 78 near spherical head 82 in a location that can sometimes be subjected to stress during installation and use. The axial length of sleeve 64 allows sizing component 62 to engage healthy cancellous bone, displacing any weak or unhealthy cancellous bone. As discussed below, shaft 78 can be provided with a stop or locking feature (e.g. stop 248 of FIG. 11) to prevent sleeve 64 from backing out of the bone bore and protruding beyond the cortical bone.

The diameter of sleeve 64 can vary in different embodiments of sizing component 62. Likewise, the length of sizing component 62 between first end 68 and second end 79 can vary in different embodiments of sizing component 62. Thus, a variety of sizing components 62 can be provided in inventory, such as in a system, set, kit or package, or as part of a surgical system, to allow a surgeon or practitioner to intra-operatively select one or more sizing components of desired length and diameter, or material to compensate for or overcome weakened or defective boney structure at a particular surgical site of a patient at a location where the procedure is performed.

Figure 4:
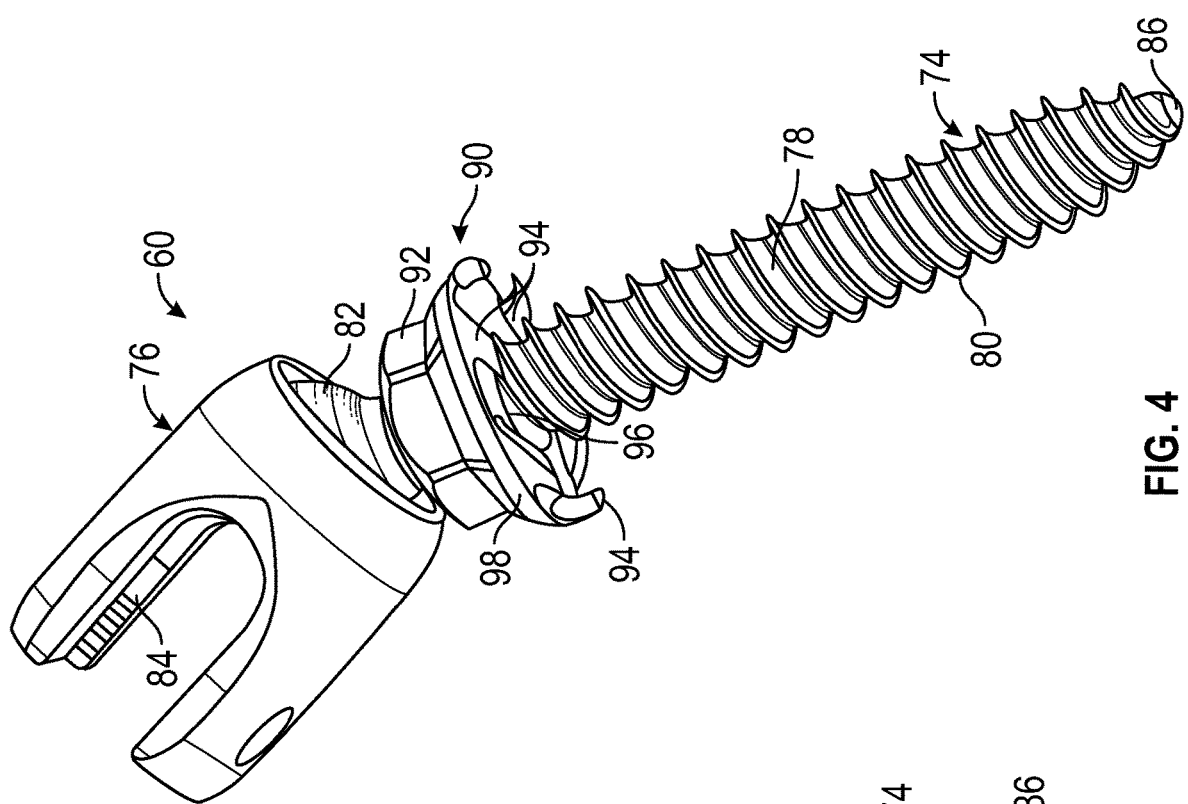
FIG. 4 is a perspective view of an exemplary bone anchor having a second embodiment of a sizing component comprising a cap disposed along a shaft of a threaded fastener and having axially extending fixation teeth.

FIG. 4 is a perspective view of exemplary bone anchor 60 having sizing component 90, which can comprise cap 92 having axial fixation teeth 94 and central bore 96. Bone anchor 60 can be configured in the same manner as described with reference to FIG. 3 and can function similarly as bone anchor 10 of FIGS. 1 and 2. Bone anchor 60 can comprise fastener 74 and housing 76, which includes slot 84. Fastener 74 can include shaft 78, which can include threading 80, head 82 and tip 86.

Sizing component 90 can be sized to mate with shaft 78 of fastener 74. For example, the outer diameter of shaft 78 can be sized to fit within the diameter of central bore 96, and internal threading within central bore 96 can be sized to mate with threading 80. Sizing component 90, however, can be configured to operate with other bone anchor devices, such as bone anchor 200 of FIGS. 7-9.

Cap 92 can extend along a central axis that is configured to be co-axial with the central axis of shaft 78. Cap 92 can have an octagonal or hexagonal outer perimeter surface shape in order to engage a driver device. As such, insertion and removal of sizing component 90 can be facilitated with an instrument such as an open end wrench. However, the shape of the outer perimeter of cap 92 can have other configurations, such as square or circular.

Cap 92 can have an outer perimeter size selected to increase the diameter or size of shaft 78 any desirable amount to provide a larger anchoring footprint, as discussed below. In particular, fixation teeth 94 can extend from rim 98 to engage cortical bone surrounding shaft 78. Rim 98 can comprise a flange that can extend radially and/or axially from cap 92 to position fixation teeth 94 for engaging bone. Fixation teeth 94 can extend axially from rim 98 in a distal direction away from cap 92. Fixation teeth 94 can have a circumferential orientation to facilitate insertion into the cortical bone as sizing component 90 is rotated. In an example, fixation teeth 94 can be oriented in a clockwise circumferential direction when viewed from the proximal end of shaft 78 near spherical head 84 (as depicted in FIG. 4) to facilitate insertion of fixation teeth 94 when cap 92 is rotated in a clockwise or right-hand thread direction. In other examples, fixation teeth 94 can have different shapes or can be replaced with textured or jagged surfaces along rim 98 for engaging bone.

As cap 92 is threaded onto shaft 78, the outer size of cap 92 can radially increase the diameter of bone anchor 60 to allow shaft 78 to increase or enlarge the anchoring footprint of fastener 74. In particular, shaft 78 can be configured to anchor bone anchor 60 into a bone bore having approximately the same diameter as shaft 78. However, as discussed, the boney structure may be weakened or deficient such that threads 80 cannot take adequate hold in the boney structure, thereby leaving open the possibility of bone anchor 60 becoming dislodged or displaced. Cap 92 can enlarge shaft 78 such that bone anchor 60 can become engaged in bone outside of, or larger than, the diameter of shaft 78. For example, cap 92 can be selected to have an outer size that is larger than a diseased or weakened bone area surrounding a bone bore into which shaft 78 is threaded. Thus, fixation teeth 94 of cap 92 can provide anchoring in healthy or structurally sound bone material that surrounds the bone bore.

Cap 92 can be threaded onto shaft 78 up to the proximal end of threading 80 near spherical head 82. As such, cap 92 can be configured to overcome deficient boney structure proximate a cortical bone surface surrounding the bone bore. Shaft 78 continues to provide anchoring within the bone bore in cancellous bone. As discussed below, shaft 78 can be provided with a stop feature (e.g. stop 248 of FIG. 11) to prevent cap 92 from backing out from engagement with the cortical bone.

The diameter of cap 92 can vary in different embodiments of sizing component 90. Likewise, the shape, such as the length, of fixation teeth 94 can vary in different embodiments of sizing component 90. Thus, a variety of sizing components 90 can be provided in inventory, such as in a system, set, kit or package, or as part of a surgical system, to allow a surgeon or practitioner to intra-operatively select one or more sizing components of desired length and diameter to compensate for or overcome weakened or defective boney structure at a particular surgical site of a patient at a location where the procedure is performed.

Figure 5:
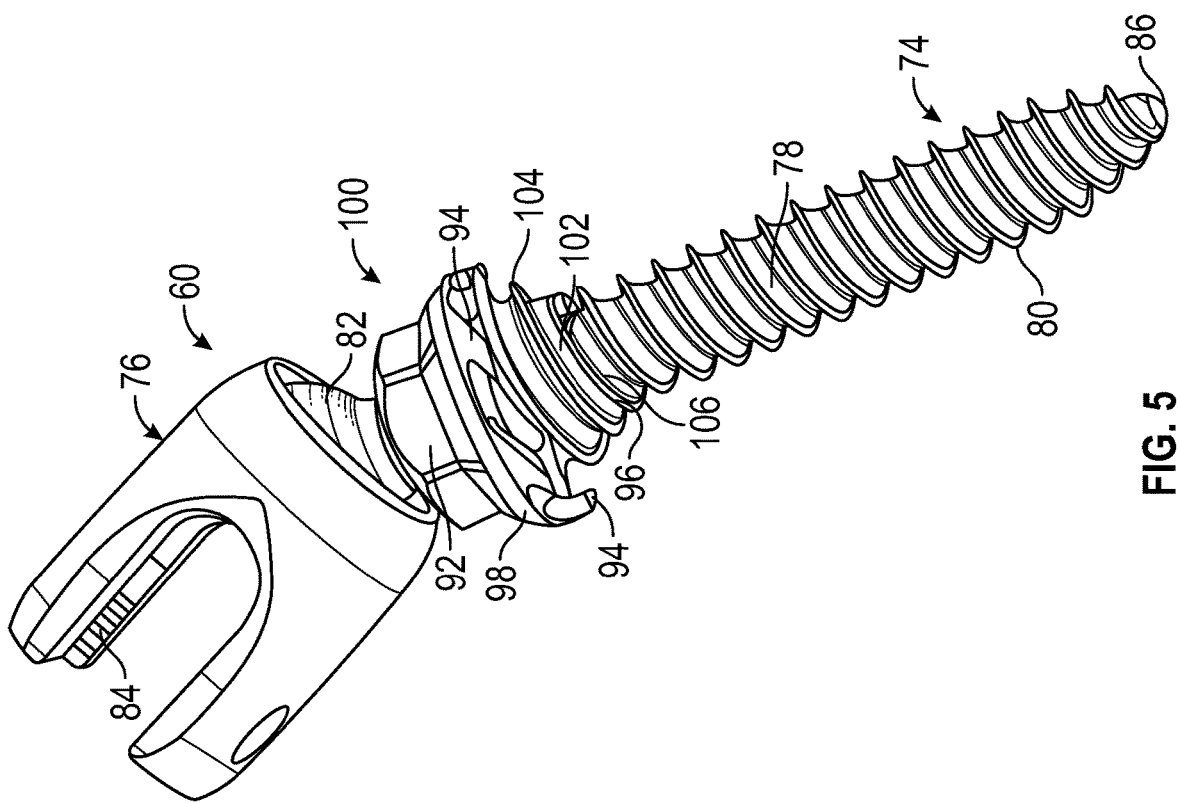
FIG. 5 is a perspective view of an exemplary bone anchor having a third embodiment of a sizing component comprising a cap having a threaded sleeve that extends along only a portion of a threaded fastener.

FIG. 5 is a perspective view of exemplary bone anchor 60 having sizing component 100, which can be configured similarly as sizing component 90 of FIG. 4 with the addition of extension sleeve 102. Sizing component 100 can also include cap 92, axial fixation teeth 94, central bore 96 and rim 98. Extension sleeve 102 can include threading 104. Bone anchor 60 can be configured in the same manner as described with reference to FIG. 3 and can function similarly as bone anchor 10 of FIGS. 1 and 2. Bone anchor 60 can comprise fastener 74 and housing 76, which includes slot 84. Fastener 74 can include shaft 78, which can include threading 80, head 82 and tip 86.

Cap 92 can function similarly as described with reference to FIG. 4. Extension sleeve 102 and threading 104 can function similarly as threaded sleeve 64 and threading 66 of sizing component 62 of FIG. 3. As such, FIG. 5 depicts a combination of the embodiments of FIGS. 3 and 4 wherein first end 68 of threaded sleeve 64 extends from cap 92.

Extension sleeve 102 can extend from cap 92 along a central axis that is configured to be co-axial with the central axis of shaft 78. Extension sleeve 102 can be tapered between cap 92 and distal end 106 in order to provide a smooth transition between the outer diameter of shaft 78 and the outer diameter of sleeve extension 102. The diameter of extension sleeve 102 can be selected to increase the diameter of shaft 78 any desirable amount to provide a larger anchoring footprint, as discussed herein. Distal end 106 can have a diameter that is just slightly larger than the outer diameter of shaft 78 sufficient to allow insertion of shaft 78 into extension sleeve 102. Thus, the diameter of extension sleeve 102 can be tapered so that, as shaft 78 is threaded into bone, sizing component 100 can be eased or gradually inserted into the bore in the boney structure. Threading 104 on extension sleeve 102 can be sized to be the same as threading 80 on shaft 78. For example, threading 104 on extension sleeve 102 can have the same pitch as threading 80 on shaft 78 to facilitate advancement into the boney structure at the same rate and prevent binding.

Sizing component 100 can comprises extension sleeve 102 that can be larger than the diameter of shaft 78, and cap 92 that can be larger than the diameter of extension sleeve 102. Thus, as sizing component 100 is threaded onto shaft 78, the outer diameter of extension sleeve 102 and threading 104 can effectively radially increase the diameter of shaft 78 to increase or enlarge the anchoring footprint of fastener 74, while cap 92 can further increase the size of the anchoring footprint. In particular, extension sleeve 102 can increase the anchoring footprint in the radial and axial directions to engage cancellous bone in a bone bore, while cap 92 and fixation teeth 94 can increase the anchoring footprint in the radial and axial directions to engage cortical bone. Thus, extension sleeve 102 can displace weak or unhealthy cancellous bone to engage healthy cancellous bone, while fixation teeth 94 can be extended radially beyond weak or unhealthy cortical bone to axially engage healthy cortical bone.

As discussed, the radial diameter of cap 92 and the axial length of teeth 94 can vary in different embodiments, and the radial diameter and axial length of extension sleeve 102 can vary in different embodiments such that different sizing components 100 can be used as components in different systems, sets, kits or packages. In the depicted example of FIG. 5, extension sleeve 102 has a length sized to only engage cancellous bone near the cortical surface of a bone bore. However, as shown in FIG. 6, extension sleeve 102 can be sized to extend along substantially all of shaft 78.

Figure 6:
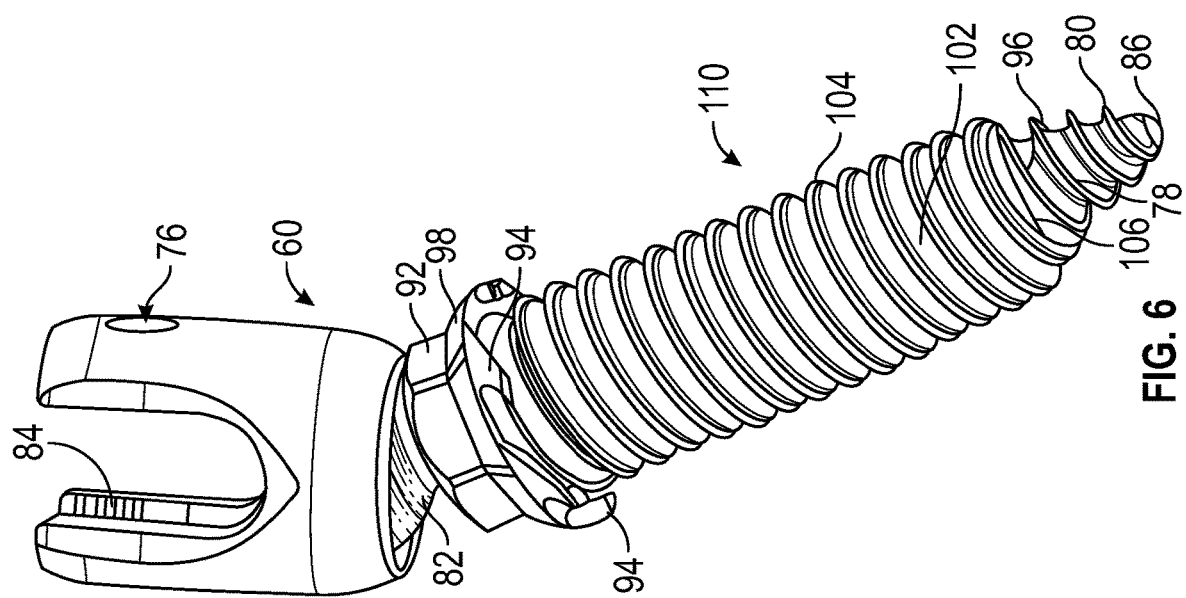
FIG. 6 is a perspective view of an exemplary bone anchor having a fourth embodiment of a sizing component comprising a cap having a threaded sleeve that extends along all but a tip portion of a threaded fastener.

FIG. 6 is a perspective view of exemplary bone anchor 60 having sizing component 110, which can be configured similarly as sizing component 100 of FIG. 4 with the addition of extension sleeve 102 having a greater length. Sizing component 110 can also include cap 92, axial fixation teeth 94, central bore 96 and rim 98. Extension sleeve 102 can include threading 104. Bone anchor 60 can be configured in the same manner as described with reference to FIG. 3 and can function similarly as bone anchor 10 of FIGS. 1 and 2. Bone anchor 60 can comprise fastener 74 and housing 76, which includes slot 84. Fastener 74 can include shaft 78, which can include threading 80, head 82 and tip 86.

As mentioned, sizing component 110 can be configured to operate in the same or a similar fashion as sizing component 100 of FIG. 5 except extension sleeve 102 is longer to engage a greater quantity of cancellous bone. Thus, distal end 106 can be positioned further down into a bone bore and the length of extension sleeve 102 can be used to displace a greater length of cancellous bone to allow threading 104 to engage a greater quantity of healthy cancellous bone. Sleeve 102 can extend across substantially all of shaft 78 except for the distal tapered end portion where tip 86 is located.

Figure 7:
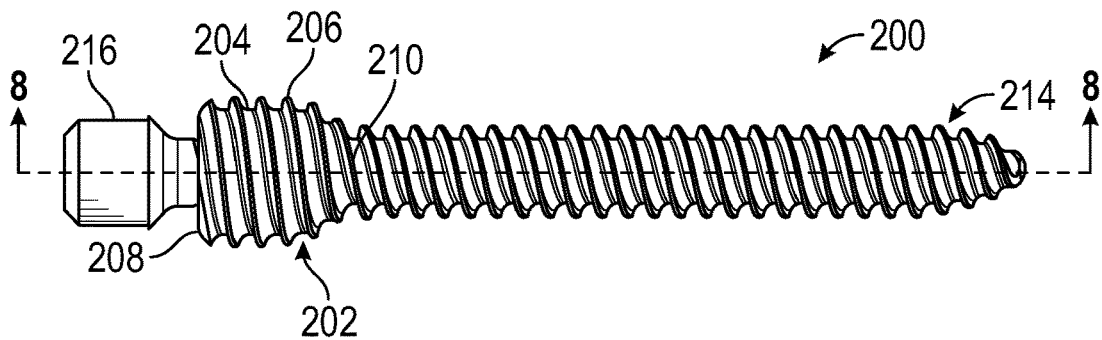
FIG. 7 is a side view of another exemplary bone anchor having a sizing component comprising a threaded sleeve.
Figure 8:
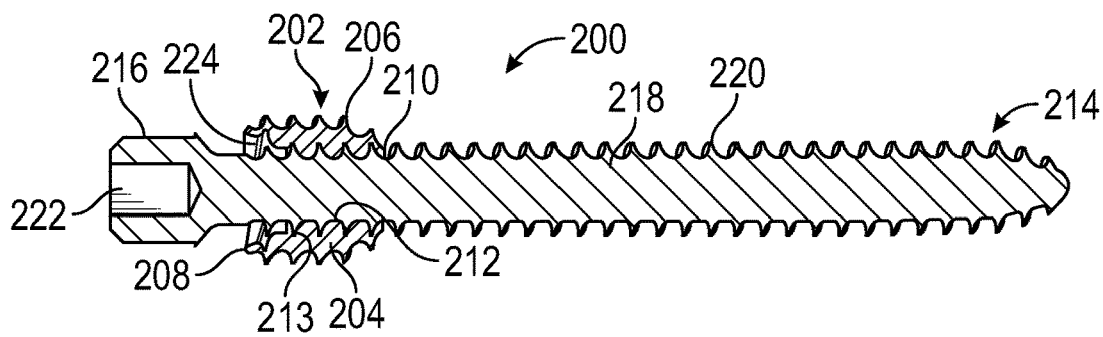
FIG. 8 is a cross-sectional view of the bone anchor and sizing component of FIG. 7.

FIG. 7 is a side view of exemplary bone anchor 200 having sizing component 202 comprising threaded sleeve 204. FIG. 8 is a cross-sectional view of bone anchor 200 and sizing component 202 of FIG. 7. FIGS. 7 and 8 are discussed concurrently. Threaded sleeve 204 can also comprise male anchor threading 206, first end 208, second end 210 and central bore 212 with female sizing threading 213. Bone anchor 200 can comprise fastener 214, which can include head 216, shaft 218, threading 220 and socket 222.

Bone anchor 200 can function similarly as bone anchor 10 of FIG. 1 and bone anchor 60 of FIG. 3, except bone anchor 200 includes head 216 instead of spherical head 82. As such, bone anchor 200 is not configured for use with housing 76 (FIG. 3). Instead, head 216 can be used with other components, such as plates, fusion systems, intra vertebral spacers and the like. Head 216 can be cylindrical for receding into another component. Head 216 can include socket 22 for receiving a drive tool, such as a screw driver or hex head wrench. In any event, fastener 214 can be used to secure bone anchor 200 to a boney structure.

Sizing component 202 can function similarly as sizing component 60 of FIG. 3. For example, sizing component 202 can have first end 208 and second end 210, with threaded sleeve 204 being tapered there-between to facilitate smooth insertion into bone. Threading 206 can be sized to match threading 220 of shaft 218 of fastener 214. In other words, threading 206 and threading 220 can have the same pitch to ensure fastener 214 and sizing component 202 advance into the boney structure at the same rate and prevent binding. Sleeve 204 can extend along a central axis that is configured to be co-axial with the central axis of shaft 218.

Sleeve 204 of sizing component 202 can enlarge the diameter of shaft 218 to radially increase the diameter of bone anchor 200 to allow shaft 218 to increase or enlarge the anchoring footprint of fastener 214. In particular, shaft 218 can be configured to anchor bone anchor 200 into a bone bore having approximately the same diameter as shaft 218. However, as discussed, the boney structure may be weakened or deficient such that threads 220 cannot take adequate hold in the boney structure, thereby leaving open the possibility of bone anchor 200 becoming dislodged or displaced. Sleeve 204 can enlarge shaft 218 such that bone anchor 200 can become engaged in bone outside of, or larger than, the diameter of shaft 218. For example, sleeve 204 can be selected to have an outer diameter that is larger than a diseased or weakened bone area surrounding a bone bore into which shaft 218 is threaded. Thus, threading 206 of sleeve 204 can provide anchoring in healthy or structurally sound bone material.

Sleeve 204 can be threaded onto shaft 218 up to the proximal end of threading 220 near head 216. As such, sleeve 204 can be configured to overcome deficient boney structure proximate a cortical bone surface surrounding the bone bore, and can be used to strengthen shaft 218. The axial length of sleeve 204 allows sizing component 202 to engage healthy cancellous bone, displacing any weak or unhealthy cancellous bone.

Figure 9:
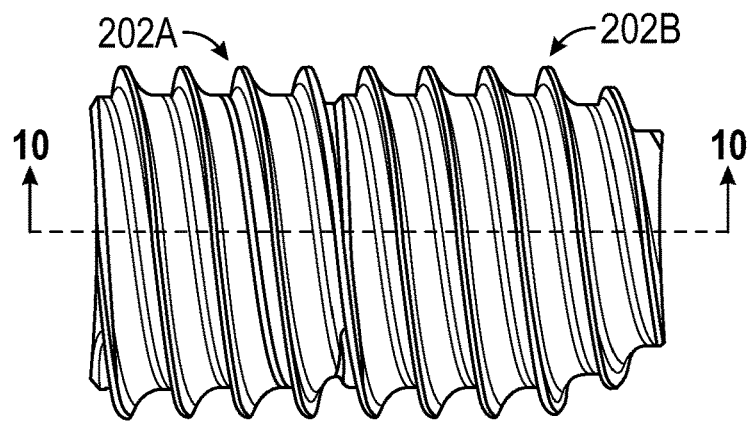
FIG. 9 is a side view of a first sizing component such as the one shown in FIGS. 7 and 8 axially abutted with a second sizing component of similar construction.
Figure 10:
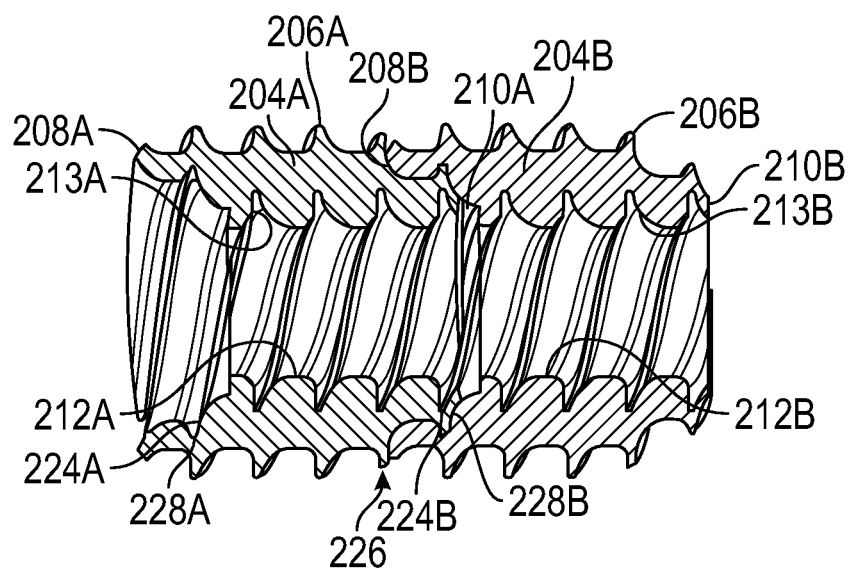
FIG. 10 is a cross-sectional view of the first and second sizing components of FIG. 9.

As with other examples and embodiments described herein, the sizes, e.g. length and diameter, of sleeve 204 can vary in different embodiments of sizing component 202 to permit a variety of sizing components 202 to be provided in inventory, such as in a system, set, kit or package, or as part of a surgical system, to allow a surgeon or practitioner to intra-operatively select one or more sizing components of desired length and diameter to compensate for or overcome weakened or defective boney structure at a particular surgical site of a patient at a location where the procedure is performed. However, first end 208 can include countersink or socket 224, which can allow for multiple sizing components 202 to be used in conjunction with each other to increase the axial anchoring footprint of sizing component 202, as shown in FIGS. 9 and 10. In other examples, socket 224 can be omitted from sizing component 202 to, for example, provide additional contact with the threaded fastener.

FIG. 9 is a side view of first sizing component 202A, such as sizing component 200 shown in FIGS. 7 and 8, axially abutted with second sizing component 202B of similar construction. FIG. 10 is a cross-sectional view of first and second sizing components 202A and 202B of FIG. 9. FIGS. 9 and 10 are discussed concurrently.

Sizing component 202A can include threaded sleeve 204A having threading 206A, first end 208A, second end 210A, central bore 212A, sizing threading 213A and socket 224A. Sizing component 202B can include threaded sleeve 204B having threading 206B, first end 208B, second end 210B, central bore 212B, sizing threading 213B and socket 224B.

As mentioned, second ends 210A and 210B can be tapered to provide smooth transitions with shaft 218 of fastener 214. Sockets 224A and 224B can be shaped in the mirror images of the tapers of second ends 210A and 210B to allow the tapering to be fully recessed into sockets 224A and 224B. For example, socket 224B can receive all or nearly all of the tapering of second end 210A such that there is no change in the diameter of the joined sizing components 202A and 202B between sleeves 204A and 204B at junction 226. Sockets 224A and 224B can include threading 228A and 228B, respectively to receive threading of a mating sizing component. For example, socket 224B of sizing component 202B can include threading 228B to receive threading 206A of sizing component 202A. Thus, multiple sizing components 202 can be axially stacked together to increase the effective length of the sizing component. This can reduce the number and variety of different sizing components needed in inventory to form different systems, sets, kits and packages as described herein.

Figure 11:
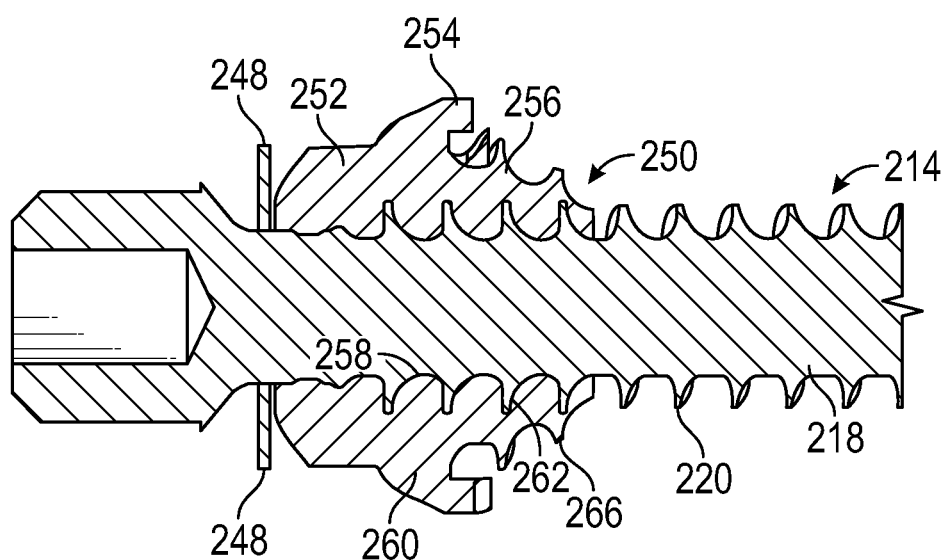
FIG. 11 is a cross-sectional view of a portion of the bone anchor of FIG. 8 having a stop and an embodiment of a sizing component having a cap with axial fixation teeth and a sleeve.

FIG. 11 is a cross-sectional view of a portion of fastener 214 of FIG. 8 having stop 248 and an exemplary sizing component 250 having cap 252 with axial fixation teeth 254 and sleeve 256. Sizing component 250 can also include central bore 258 and rim 260. Sizing component 250 is similar to sizing component 100 of FIG. 5, except being particularly sized for use with fastener 214. As such, central bore 258 can be sized to receive the diameter of shaft 218 of fastener 214, and central bore 258 can include female sizing threading 262 to receive male anchor threading 220 of shaft 218. However, as discussed, any of the sizing components described herein can have different dimensions in different embodiments for use with a variety of different fasteners and bone anchors.

Cap 252 can be shaped to have surfaces to engage a drive tool, such as a wrench or the like. Rim 260 can extend from cap 252 to position teeth 254 radially outward of sleeve 256. Rim 260 can extend radially outward from cap 252 and axially away from cap 252. Teeth 254 can extend axially from rim 260 to provide axial anchoring in bone surrounding fastener shaft 218. Sleeve 256 can extend axially from cap 252 within teeth 254. Sleeve 256 increases the diameter of shaft 218 such that threading 266 of sleeve 256 can increase the anchoring footprint of fastener 214 beyond what is provided by threading 220. Sleeve 256 and threading 266 can be shaped to smoothly mate with shaft 218 and threading 220. For example, sleeve 256 can be tapered to allow for a smooth entry of shaft 218 and sizing component 250 into a bone bore. Also, threading 266 can have the same pitch as threading 220 to allow for entry of shaft 218 and sizing component 250 into a bone bore without binding.

The various embodiments and examples of sizing components described herein can be made of a variety of different materials in different embodiments. In an example, the sizing components can be made of porous metal or biocompatible metal or alloys. In particular examples, the sizing components can be made from titanium or Trabecular Metal™, which is commercially available from Zimmer Inc. In other examples, the sizing components can be made of a polymer, such as polyether ether ketone (PEEK). In yet other examples, the sizing components can be made of autograft or allograft bone.

Figure 12:
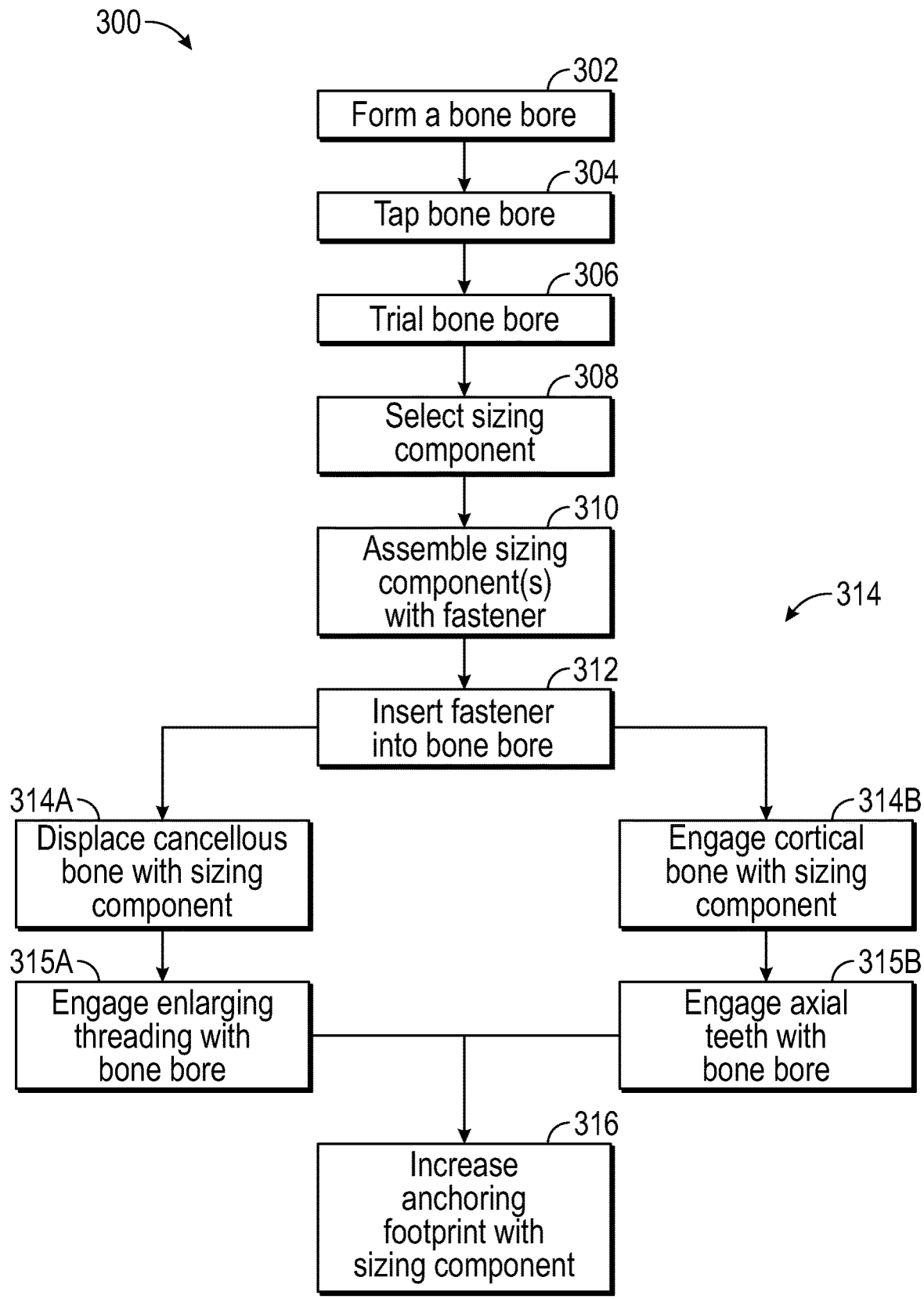
FIG. 12 is a flow chart diagramming a method of implanting a sizing component of the present application.

FIG. 12 is a flow chart diagramming method 300 of implanting a sizing component of the present application.

Method 300 can include the steps of forming a bone bore in a boney structure 302, tapping the bone bore 304, trialing the bone bore 306, selecting a sizing component for use in the bone bore 308, assembling the sizing component with a fastener 310, inserting the fastener into the bone bore 312, engaging one or more portions of the sizing component with the boney structure 314 and increasing the anchoring footprint of the fastener with the sizing component 316.

Forming a bone bore at step 302 can comprise producing a bore or hole within a boney structure for receiving a bone anchor. A drill or an awl can be used to produce a channel through cortical bone and into cancellous bone. The bone bore can have a diameter that substantially matches the diameter of a fastener, such as a threaded fastener. As such, the diameter of the bone bore can be sized to accommodate threading of a fastener shaft.

Tapping the bone bore at step 304 can comprise using a thread tap to produce threading in the bone bore to match the threading of a desired threaded fastener of a bone anchor to be used in the bone bore. Any conventional thread tap can be used. In other examples, the bone bore may not be pre-threaded. As such, self-tapping bone fasteners can be used.

Trialing the bone bore at step 306 can comprise assessing the quality of bone at and around the bone bore via a variety of means. For example, the bone bore can be visually inspected by the surgeon or practitioner to assess the extent of damaged or unhealthy bone in and around the bone bore. Additionally, various instruments can be inserted into the bone bore to determine the extent of unhealthy or damaged bone. For example, a probe can be inserted into the bone bore to allow the surgeon or practitioner to feel the depth of any bone damage. Additionally, a bone anchor may be inserted into the bone bore to evaluate the effectiveness of a fastener used with the bone anchor. For example, a threaded fastener can be inserted or screwed into the bone bore and the surgeon or practitioner can tactilely feel if the fastener provides adequate anchoring support.

Selecting a sizing component at step 308 can comprise using information determined during trialing of the bone bore at step 306 to select one or more of the various sizing components described herein. For example, the radius of any damaged or unhealthy bone surrounding the bone bore can be used to select a sizing component of adequate diameter, and the depth of any damaged or unhealthy bone into the bone bore can be used to select a sizing component of adequate length.

Assembling the sizing component with the fastener at step 310 can comprise connecting the selected sizing component to the selected bone anchor. For example, a fastener of the selected bone anchor can be inserted or threaded into a sleeve or cap of a selected sizing component. In other examples, the sizing component can be connected to the fastener by other mechanisms. In yet other examples, the sizing component can be inserted into the bone first and the fastener can be passed through the sizing component second.

Inserting the fastener into the bone bore at step 312 can comprise threading the shaft of the fastener of the bone anchor into the bone bore. The shaft can be partially inserted into the bone bore before any sizing component engages boney structure of the bone bore. Alternatively, the sizing component can be initially threaded into the bone bore such that the fastener does not actually contact the bone bore.

The fastener can be advanced such that the sizing component engages the bone structure at step 314. The sizing component can engage the boney structure in a variety of different ways. In an example, the sizing component can be used to displace cancellous bone within the bone bore at step 314A, which can be accomplished by engaging enlarging threading of the sizing component, such as that disposed on a sleeve surrounding the shaft of the threaded fastener, with cancellous bone in the bone bore at step 315A. In an example, the sizing component can be used to engage cortical bone surrounding the bone bore at step 314B, which can be accomplished by engaging axially extending teeth of the sizing component, such as teeth that extend from a rim surrounding a cap surrounding the shaft of the threaded fastener, to engage cortical bone surrounding the bone bore at step 315B. Additionally, sizing components can be configured to engage both cortical and cancellous bone such that steps 315A and 315B can be achieved concurrently (or in quick succession as the fastener with the sizing component is advanced into the bone). As a result of step 314, the anchoring footprint of the bone anchor can be increased with the sizing component(s) at step 316. As such, the bone anchor can be more securely held in place in the bone bore with a reduced risk of becoming displaced.

FIG. 13 is a side view of exemplary bone anchor 400 including fastener 402 having first external thread pitch P1 and sizing component 404 having second external thread pitch P2. Sizing component 404 can comprise threaded sleeve 406 having threading 408 extending between first end 410 and second end 412 of threaded sleeve 406. Fastener 402 can comprise head 414 and shaft 416. Shaft 416 can include threading 418 that extends between a tip (not shown) and head 414.

Bone anchor 400 can operate similarly to bone anchor 200 of FIG. 7 with the exception that threading 418 can be at a different pitch than threading 220. In particular, threading 408 can be dual lead and threading 418 can be single lead with double pitch. Threading 418 can be configured to have large, deep valleys and can be widely-spaced between threading to provide for deep anchoring in cancellous bone structure. Threading 408 can be configured to have small, shallow valleys and can be closely-spaced to provide abundant anchoring in cortical bone. In one example, pitch P1 can be approximately 3.0 mm and pitch P2 can be approximately 1.5 mm.

FIG. 14 is a perspective view of a poly-axial bone anchor 500 having threaded sleeve 502 configured to pivotably and rotationally lock housing 504 relative to fastener 506. Threaded sleeve 502 can comprise sleeve portion 508 and cup portion 510.

Housing 504 can comprise a generally U-shaped body having passage 512 into which a stabilization rod can be placed. Passage 512 can be threaded to receive a closure member, such as closure member 11, in order to lock the stabilization rod into housing 504. As shown in FIG. 15, fastener 506 can include spherical or semi-spherical head 514 that can be positioned within housing 504. Housing 504 can thus be configured to poly-axially pivot with respect to the longitudinal axis of fastener 506. Housing 504 can also rotate three-hundred-sixty degrees about the longitudinal axis of fastener 506. As discussed in greater detail below, sleeve portion 508 can be threaded up the shank of fastener 506 to push cup portion 510 into engagement with housing 504. Cup portion 510 can be configured to convert poly-axial bone anchor 500 into a mono-screw bone anchor, e.g., a bone anchor where housing 504 is fixed in a single position relative to fastener 506.

FIG. 15 is a top view of poly-axial bone anchor 500 of FIG. 14 showing cup portion 510 of threaded sleeve 504 engaging housing 504. Cup portion 510 can include high-sides 516 and low-sides 518. Housing 504 can include flat, rod passage-sides 520 and rounded, distractor-sides 522. Distractor-sides 522 can include sockets 524 which can be configured to receive an instrument, such as a distractor, to manipulate housing 504 and bone anchor 500.

Figure 16:
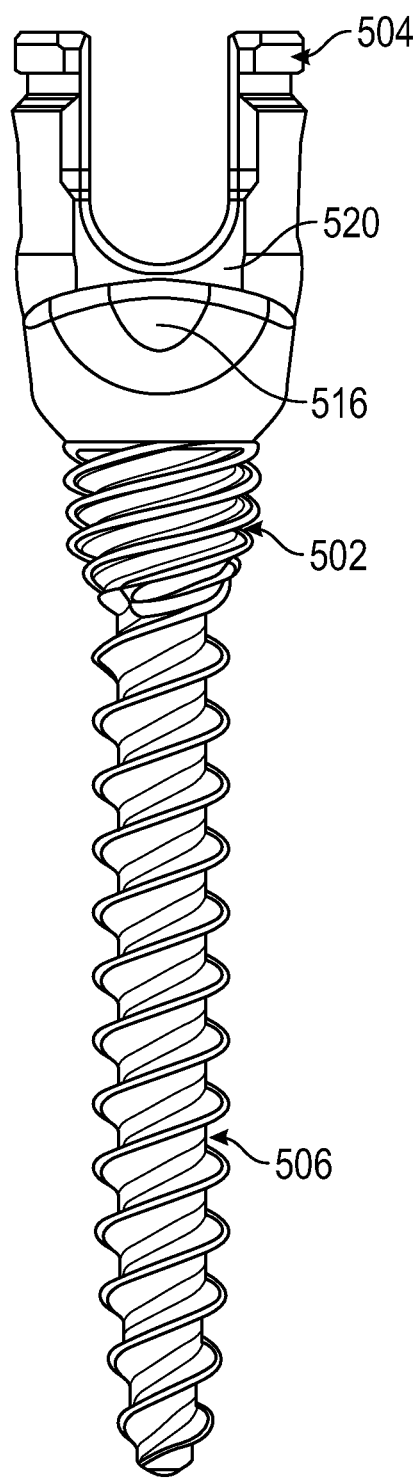
FIG. 16 is a front view of the poly-axial bone anchor of FIG. 14 showing a high-side of the cup engaging a rod-passage side of the housing.
Figure 17:
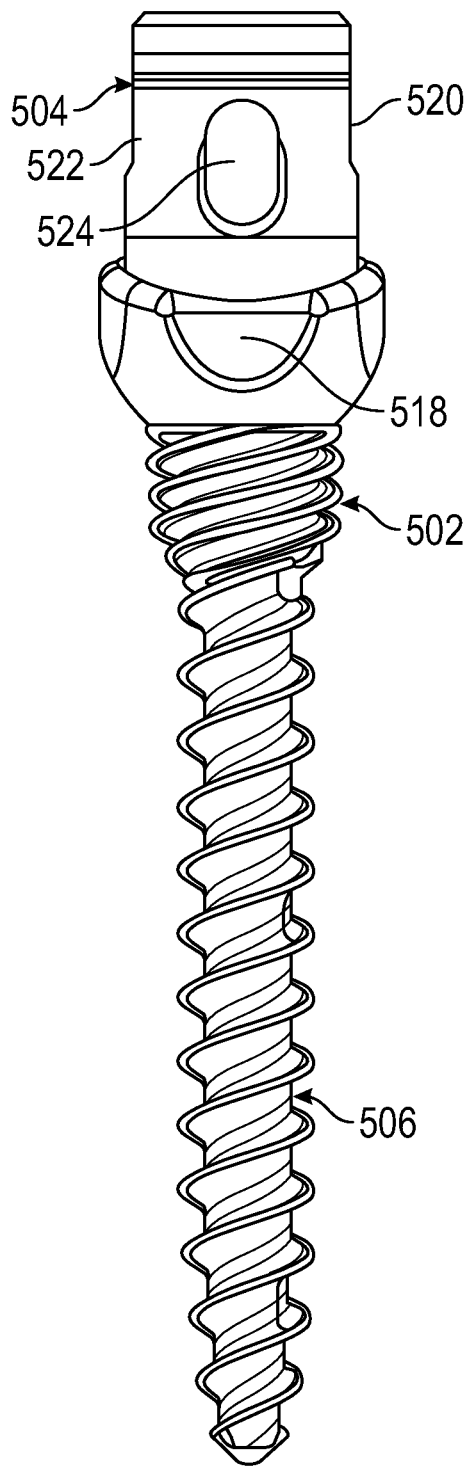
FIG. 17 is a side view of the poly-axial bone anchor of FIG. 14 showing a low-side of the cup engaging a distractor side of the housing.

FIG. 16 is a front view of the poly-axial bone anchor 500 of FIG. 14 showing a high-side 516 of cup portion 510 engaging a rod-passage side 520 of housing 504. FIG. 17 is a side view of poly-axial bone anchor 500 of FIG. 14 showing low-side 518 of cup portion 510 engaging distractor-side 522 of housing 504.

Figure 18:
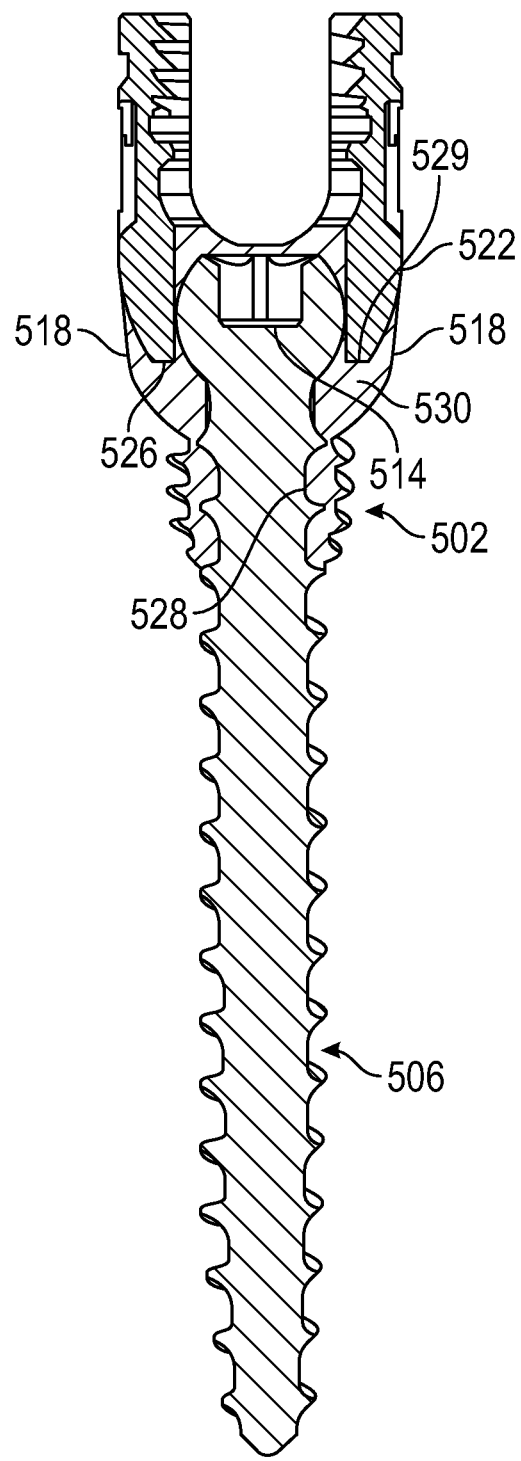
FIG. 18 is a cross-sectional view of the poly-axial bone anchor of FIG. 15 taken at section 18-18 showing the low-side of the cup engaging a curved portion of the housing.
Figure 19:
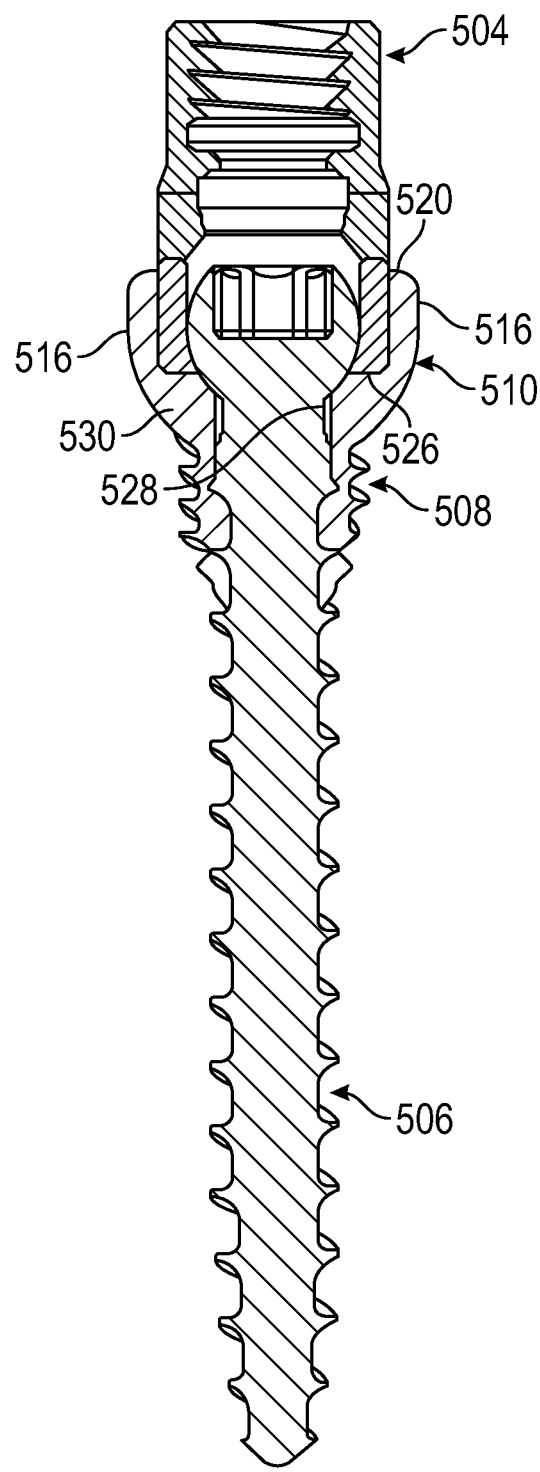
FIG. 19 is a cross-sectional view of the poly-axial bone anchor of FIG. 15 taken at section 19-19 showing the high-side of the cup engaging a flat portion of the housing.

FIG. 18 is a cross-sectional view of poly-axial bone anchor 500 of FIG. 15 taken at section 18-18 showing low-side 518 of cup portion 510 engaging housing 504. FIG. 19 is a cross-sectional view of poly-axial bone anchor 500 of FIG. 15 taken at section 19-19 showing high-side 516 of cup portion 510 engaging housing 504.

As shown in FIGS. 18 and 19, housing 504 can also include a lower surface 526 that can be generally flat in a plane perpendicular to the axis of fastener 506. Sleeve portion 508 can include internal bore 528 that can be advanced along the shank of fastener 506. For example, threading on fastener 506 can be used to forcibly push a flat surface 529 of cup portion 510 against surface 526 to thereby apply an anti-pivoting force against housing 504. Additionally, high-sides 516 and low-sides 518 extend up along rod passage-sides 520 and distractor-sides 522, respectively, of housing 504 to prevent angulation or pivoting of housing 504 relative to fastener 506. Engagement of high-sides 516 of cup portion 510 with rod passage-sides 520 of housing 504 and engagement of low-sides 518 of cup portion 510 with distractor-sides 522 can form a multi-faceted engagement, similar to a hex head bolt and wrench configuration, which can also prevent rotation of housing 504 relative to fastener 506 simultaneously with preventing pivoting.

High-sides 516 and low-sides 518 of cup portion 510 can extend from lower bowl portion 530. As shown in FIGS. 20-25, high-sides 516 and low-sides 518 can be omitted from cup portion 510 so that threaded sleeve 502 can be configured to only prevent angulation or pivoting of housing 504 relative to fastener 506, while permitting rotation of housing 504 relative to fastener 506.

Figure 20:
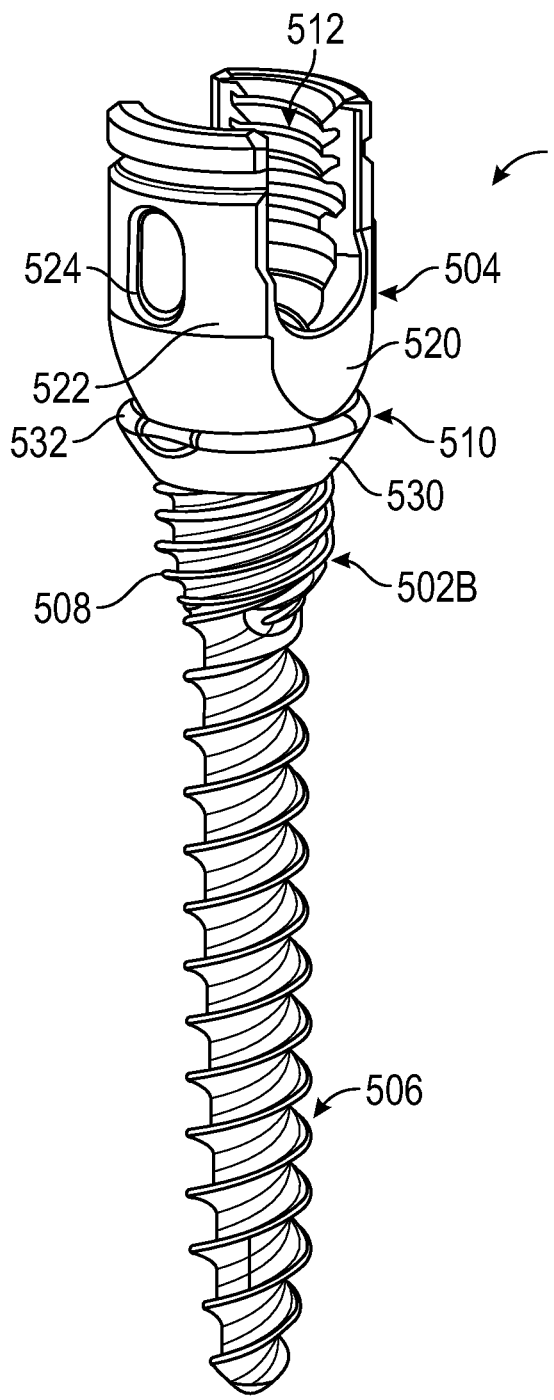
FIG. 20 is a perspective view of a poly-axial bone anchor having a threaded sleeve configured to pivotably lock a housing relative to a fastener.
Figure 21:
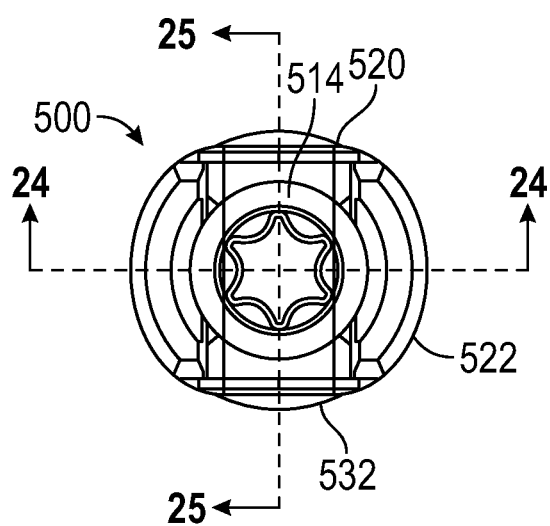
FIG. 21 is a top view of the poly-axial bone anchor of FIG. 20 showing an axi-symmetric cup of the threaded sleeve engaging the housing.

FIG. 20 is a perspective view of poly-axial bone anchor 500 having threaded sleeve 502B configured to pivotably lock housing 504 relative to fastener 506. FIG. 21 is a top view of poly-axial bone anchor 500B of FIG. 20 showing cup portion 510 of threaded sleeve 502B having axi-symmetric bowl portion 530 engaging housing 504.

Figure 22:
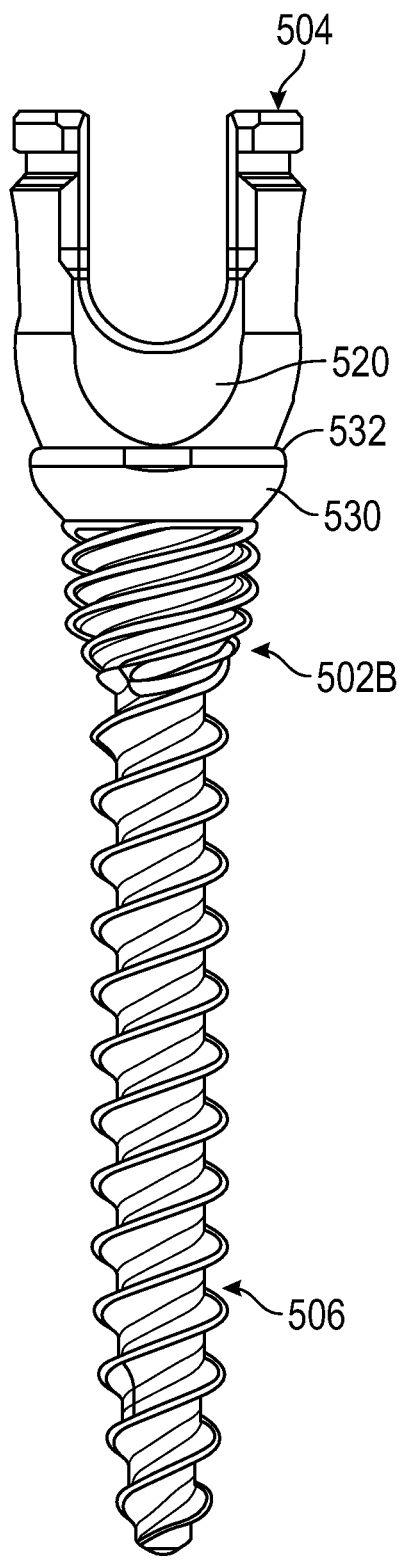
FIG. 22 is a front view of the poly-axial bone anchor of FIG. 20 showing a rim of the axi-symmetric cup engaging a rod-passage side of the housing.
Figure 23:
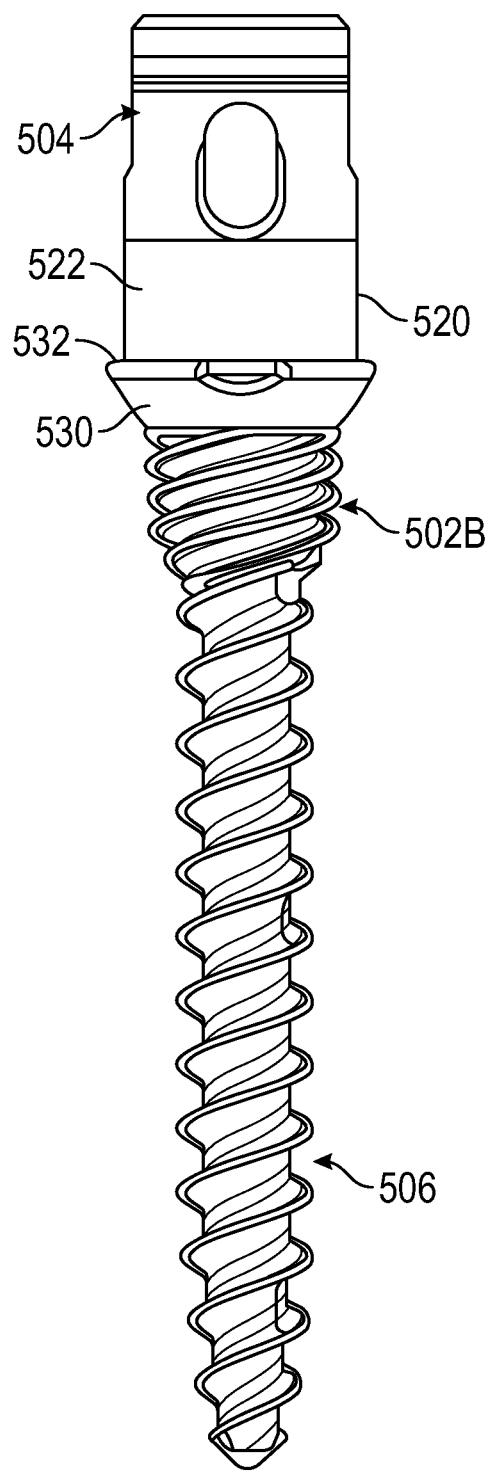
FIG. 23 is a side view of the poly-axial bone anchor of FIG. 20 showing the rim of the axi-symmetric cup engaging a distractor side of the housing.

FIG. 22 is a front view of poly-axial bone anchor 500 of FIG. 20 showing rim 532 of axi-symmetric bowl portion 530 engaging rod-passage side 520 of housing 504. FIG. 23 is a side view of the poly-axial bone anchor of FIG. 20 showing rim 532 of axi-symmetric bowl portion 530 engaging distractor side 522 of housing 504.

Figure 24:
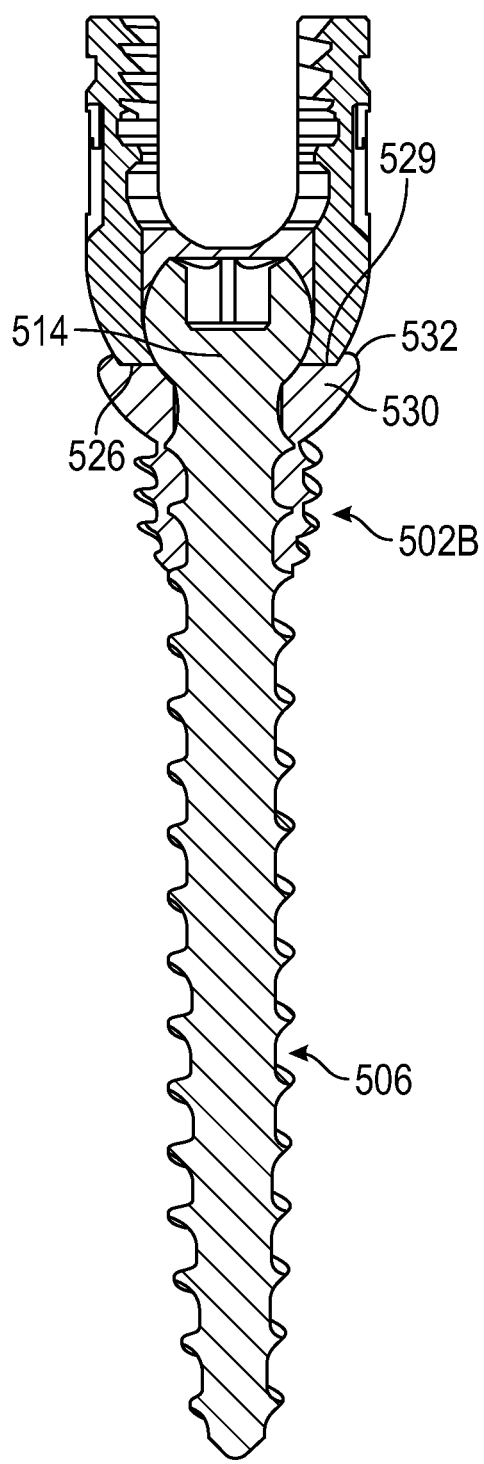
FIG. 24 is a cross-sectional view of the poly-axial bone anchor of FIG. 21 taken at section 24-24 showing the rim of the cup engaging a rim surface of the housing.
Figure 25:
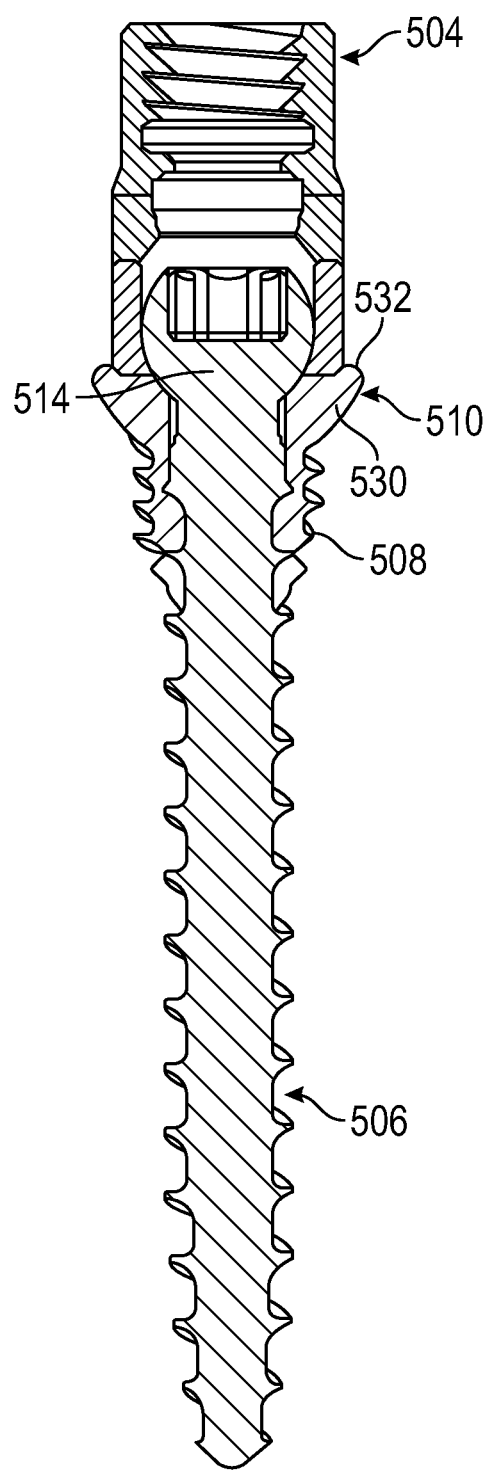
FIG. 25 is a cross-sectional view of the poly-axial bone anchor of FIG. 21 taken at section 25-25 showing the rim of the cup engaging a rim surface of the housing.

FIG. 24 is a cross-sectional view of poly-axial bone anchor 500 of FIG. 21 taken at section 24-24 showing rim 532 of bowl portion 530 engaging rim surface 526 of housing 504. FIG. 25 is a cross-sectional view of poly-axial bone anchor 500 of FIG. 21 taken at section 25-25 showing rim 532 of bowl portion 530 engaging rim surface 526 of housing 504.

FIGS. 20-25 include the same references numbers as FIGS. 14-19 with the exception of high-sides 516 and low-sides 518 being replaced with rim 532. In other words, rim 532 projects axially from bowl portion 530 instead of high-sides 516 and low-sides 518. In an embodiment, rim 532 extends three-hundred-sixty degrees around bowl portion 530.

As with threaded sleeve 502 of FIG. 14, threaded sleeve 502B of FIG. 20 includes flat surface 529 that can be pushed against surface 526 of housing 504 to inhibit pivoting of housing 504 relative to fastener 506. However, rim 532 does not project far enough to engage rod passage-sides 520 and distractor-sides 522, thereby not interfering with the ability of housing 504 to rotate about the longitudinal axis of fastener 506.

Figure 26:
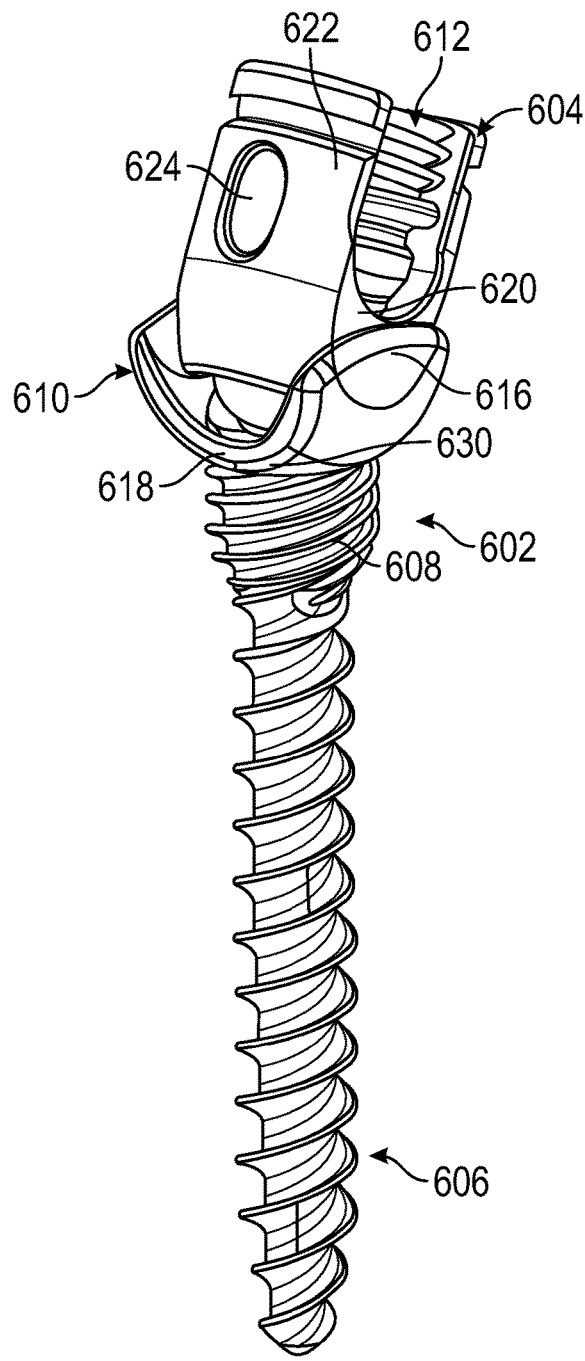
FIG. 26 is a perspective view of a poly-axial bone anchor having a threaded sleeve configured to uni-planarly lock a housing relative to a fastener.

FIG. 26 is a perspective view of poly-axial bone anchor 600 having threaded sleeve 602 configured to uni-planarly lock housing 604 relative to fastener 606. Threaded sleeve 602 can comprise sleeve portion 608 and saddle portion 610.

Housing 604 and fastener 606 can be configured similarly as housing 504 and fastener 506 of FIGS. 14-19. Further discussion is omitted here except to say that with respect to housing 604 and fastener 606, 500 series reference numbers are replaced with 600 series reference numbers.

Figure 27:
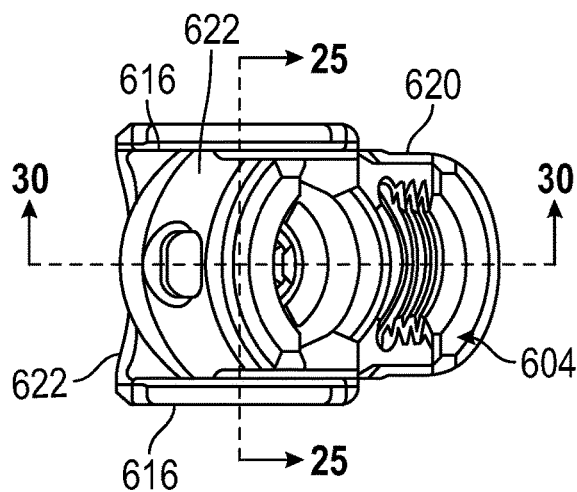
FIG. 27 is a top view of the poly-axial bone anchor of FIG. 26 showing a saddle of the threaded sleeve engaging the housing.

FIG. 27 is a top view of poly-axial bone anchor 600 of FIG. 26 showing saddle portion 610 of threaded sleeve 602 engaging housing 604.

Saddle portion 610 can include high-sides 616 and low-sides 618. Housing 604 can include flat, rod passage-sides 620 and rounded, distractor-sides 622. Distractor-sides 622 can include sockets 624 which can be configured to receive an instrument, such as a distractor, to manipulate housing 604 and bone anchor 600.

Figure 28:
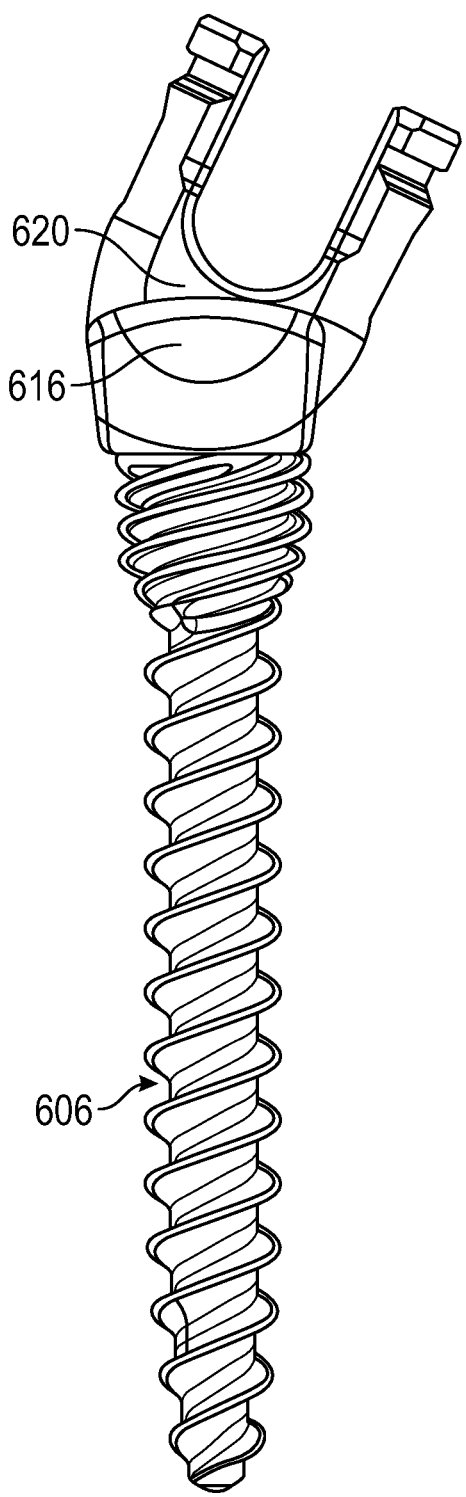
FIG. 28 is a front view of the poly-axial bone anchor of FIG. 26 showing a high-side of the saddle engaging a rod-passage side of the housing.
Figure 29:
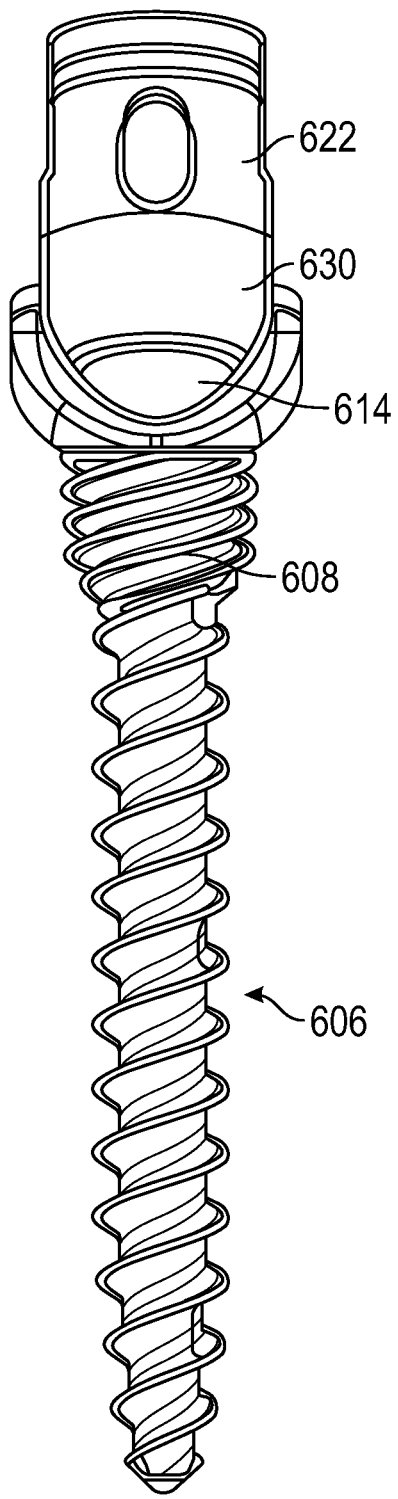
FIG. 29 is a side view of the poly-axial bone anchor of FIG. 26 showing a low-side of the saddle disengaging a distractor side of the housing.

FIG. 28 is a front view of poly-axial bone anchor 600 of FIG. 26 showing high-side 616 of saddle portion 610 engaging rod-passage side 620 of housing 604. FIG. 29 is a side view of poly-axial bone anchor 600 of FIG. 26 showing low-side 618 of saddle portion 610 disengaging distractor-side 622 of housing 604.

Figure 30:
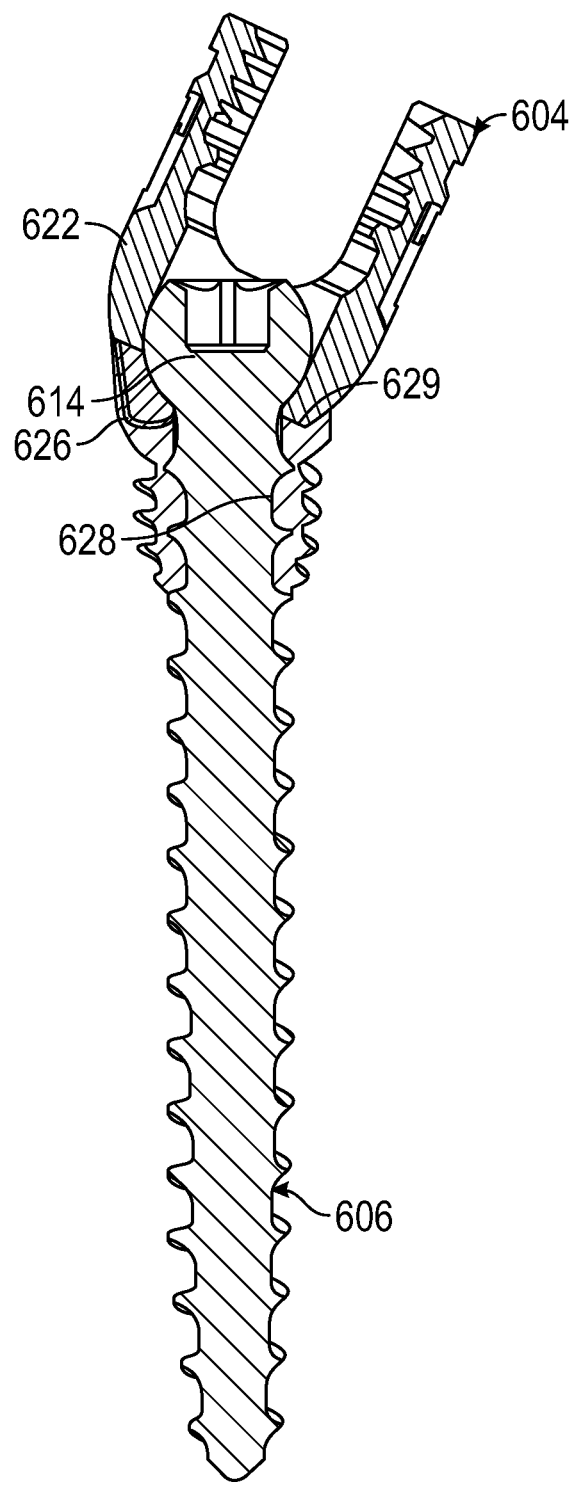
FIG. 30 is a cross-sectional view of the poly-axial bone anchor of FIG. 27 taken at section 30-30 showing the low-side of the saddle disengaging the housing.

FIG. 30 is a cross-sectional view of poly-axial bone anchor 600 of FIG. 27 taken at section 30-30 showing low-side 618 of saddle portion 610 disengaging housing 604. FIG. 31 is a cross-sectional view of poly-axial bone anchor 600 of FIG. 27 taken at section 31-31 showing high-side 616 of saddle portion 610 engaging flat portion of housing 604.

As shown in FIGS. 30 and 31, housing 604 can also include lower surface 626 that can be generally flat in a plane perpendicular to the axis of fastener 606. Sleeve portion 608 can include internal bore 628 that can be advanced along the shank of fastener 606. For example, threading on fastener 606 can be used to forcibly push a notched surface 629 of cup portion 610 against surface 626 to thereby apply an anti-rotation force against housing 604. Additionally, high-sides 616 extend up along rod passage-sides 620 of housing 504 to prevent angulation or pivoting of housing 504 relative to fastener 506 in a single bi-axial, or uni-planar, direction (e.g., movement along one axis in two directions), specifically the axial direction extending perpendicular to the planes of flat, rod passage-sides 620. High-sides 616 can also prevent rotation of housing 604. However, low-sides 618 do not extend up from bowl portion 630 to prevent angulation or pivoting of housing 604. Thus, housing 604 is permitted to move in a single bi-axial direction (e.g., along a single axis in two directions) that is parallel to the planes of flat, rod passage-sides 620. Notched surface 629 can be notched to permit this angulation of housing 604.

In another embodiment, only a single high-side 616 can extend from lower bowl portion 630. As shown in FIGS. 32-37, one of high-side 616 can be omitted from cup portion 610 so that threaded sleeve 602 can be configured to only prevent angulation or pivoting of housing 604 relative to fastener 606 in one direction, while permitting angulation or pivoting in three directions.

Figure 33:
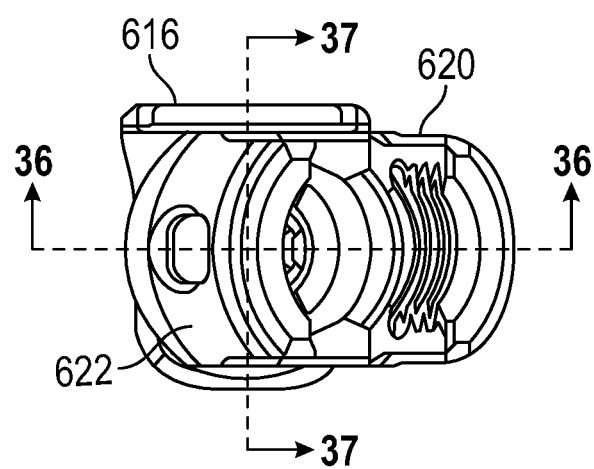
FIG. 33 is a top view of the poly-axial bone anchor of FIG. 32 showing a saddle of the threaded sleeve engaging the housing.

FIG. 32 is a perspective view of poly-axial bone anchor 600 having threaded sleeve 602B configured to uni-directionally, or uni-axially (e.g., movement along one axis in one direction), lock housing 604 relative to fastener 606. FIG. 33 is a top view of poly-axial bone anchor 600 of FIG. 32 showing saddle portion 610 of threaded sleeve 602B engaging housing 604.

Figure 34:
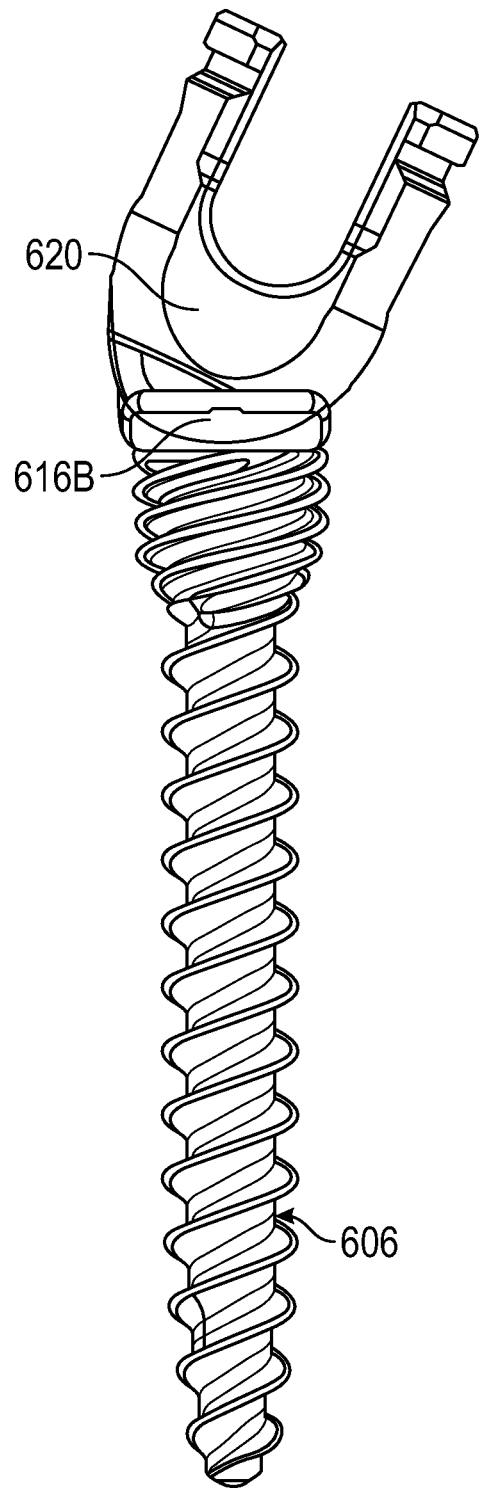
FIG. 34 is a front view of the poly-axial bone anchor of FIG. 32 showing a low-side of the saddle disengaging a rod-passage side of the housing.

FIG. 34 is a front view of poly-axial bone anchor 600 of FIG. 32 showing truncated-side 616B of saddle portion 610 disengaging rod-passage side 620 of housing 604. FIG. 35 is a side view of poly-axial bone anchor 600 of FIG. 32 showing high-side 616 of saddle portion 610 engaging rod passage side 620 of housing 604.

Figure 37:
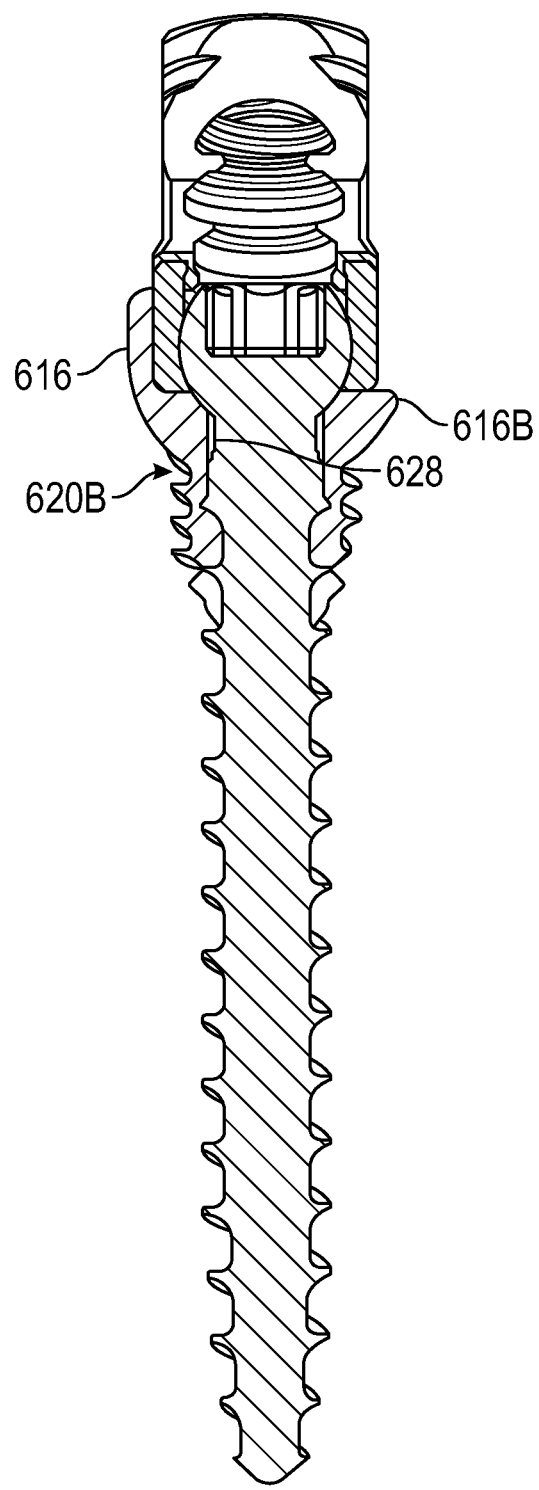
FIG. 37 is a cross-sectional view of the poly-axial bone anchor of FIG. 33 taken at section 37-37 showing a single high-side of the saddle engaging a single flat portion of the housing.

FIG. 36 is a cross-sectional view of poly-axial bone anchor 600 of FIG. 33 taken at section 36-36 showing truncated-side 616B of saddle portion 610 disengaging housing 604. FIG. 37 is a cross-sectional view of poly-axial bone anchor 600 of FIG. 33 taken at section 37-37 showing single high-side 616 of saddle portion 610 engaging a single, flat, rod passage-side 620 of housing 604.

FIGS. 32-37 include the same references numbers as FIGS. 26-31 with the exception of one of high-sides 616 being shortened to form truncated-side 616B. In an embodiment, truncated-side 616B does not extend from bowl portion 630 far enough to interfere with angulation or pivoting of housing 604.

As with threaded sleeve 602 of FIG. 26, threaded sleeve 602B of FIG. 32 includes flat surface 629 that can be pushed against surface 626 of housing 604 to inhibit pivoting and rotation of housing 604 relative to fastener 606. However, rim truncated-side 616B does not project far enough to engage one of rod passage-sides 620, thereby not interfering with the ability of housing 604 to pivot in that direction. As such, housing 604 can pivot in three uni-axial directions and is inhibited from pivoting in a fourth uni-axial direction.

Methods of using the threaded sleeves of FIGS. 14-37 can include preoperatively and intraoperatively evaluating a patient such as via reviewing images of the patient or tissue and bone of the patient. The evaluation can be used to determine how many fixed bone anchors are desired, how many mono-axial bone anchors are desired, how many uni-axial bone anchors are desired and how many poly-axial bone anchors are desired to implant a particular device or system, such as a spinal stabilization system. As such, the threaded sleeves, cups and saddles of the present application can be preoperatively and intraoperatively engaged with shafts of fasteners to provide the desired interaction with a housing. The sleeves, cups and saddles can be threaded or slid up a shaft of a fastener until walls of the sleeve, cup or saddle engage walls or surfaces of the housing to provide the desired rotational or directional limiting, or combinations thereof. As such, a hospital or other medical facility may only keep fewer types of bone anchors or only one type of bone anchor, e.g., fastener and housing combination, in stock, such as a universal, multi-axis, multi-rotational bone anchor. Smaller, less expensive sleeves and housing limiters can be kept in stock to reduce inventory size and cost.

Any of the features of the devices of FIGS. 14-37 can be combined with the features of the devices of FIGS. 1-13 in various embodiments.

VARIOUS NOTES & EXAMPLES

Example 1 can include or use subject matter such as a bone anchor system that can comprise a fastener, a rod housing and a first directional component. The fastener can comprise a shaft having a shaft diameter, an anchoring projection on the shaft, and a head at an end of the shaft. The rod housing can be connected to the head of the fastener. The first directional component can be configured for connection to the fastener. The first directional component can comprise a first body portion that can have a first outer diameter larger than the shaft diameter, a first bore that can extend through the first body portion, the first bore sized to receive the shaft diameter, and a first locking component that can extend from the first body portion configured to engage the rod housing to limit movement of the housing.

Example 2 can include, or can optionally be combined with the subject matter of Example 1, to optionally include a first locking component that can comprise a cup.

Example 3 can include, or can optionally be combined with the subject matter of one or any combination of Examples 1 or 2 to optionally include a cup that can be configured to prevent rotation and pivoting of the rod housing relative to the fastener.

Example 4 can include, or can optionally be combined with the subject matter of one or any combination of Examples 1 through 3 to optionally include a cup that can comprise a high-side and a low-side.

Example 5 can include, or can optionally be combined with the subject matter of one or any combination of Examples 1 through 4 to optionally include a rod housing that can comprise a flat side configured to engage the high-side and a curved side configured to engage the low-side.

Example 6 can include, or can optionally be combined with the subject matter of one or any combination of Examples 1 through 5 to optionally include a cup that can be configured to prevent pivoting of the rod housing relative to the fastener.

Example 7 can include, or can optionally be combined with the subject matter of one or any combination of Examples 1 through 6 to optionally include a cup that can be circumferentially symmetric.

Example 8 can include, or can optionally be combined with the subject matter of Example 1 to optionally include a first locking component that can comprises a saddle.

Example 9 can include, or can optionally be combined with the subject matter of one or any combination of Examples 1 and 8 to optionally include a saddle that can be configured to prevent pivoting of the rod housing relative to the fastener in a single plane.

Example 10 can include, or can optionally be combined with the subject matter of one or any combination of Examples 1, 8 and 9 to optionally include a saddle that can comprise a pair of high-sides and a pair of low-sides.

Example 11 can include, or can optionally be combined with the subject matter of one or any combination of Examples 1 and 8 through 10 to optionally include a rod housing that can comprise a pair of flat sides configured to engage the pair of high-sides and a pair of curved sides configured to engage the pair of low-sides.

Example 12 can include, or can optionally be combined with the subject matter of one or any combination of Examples 1, 8 and 9 to optionally include a saddle that can comprise a high-side, a truncated high-side and a pair of low-sides.

Example 13 can include, or can optionally be combined with the subject matter of one or any combination of Examples 1, 8, 9 and 12 to optionally a rod housing that can comprise a first flat side configured to engage the high-side, a second flat side configured to disengage the truncated high-side and a pair of curved sides configured to engage the pair of low-sides.

Example 14 can include or use subject matter such as a bone anchor directional component that can comprise a first body portion having a first outer diameter larger than the shaft diameter, a first bore extending through the first body portion, the first bore sized to receive a shaft of a bone anchor, and a first locking component extending from the first body portion configured to engage a rod housing of the bone anchor to limit movement of the housing relative to a fastener shaft.

Example 15 can include, or can optionally be combined with the subject matter of Example 14, to optionally include a first locking component that can comprise a cup.

Example 16 can include, or can optionally be combined with the subject matter of one or any combination of Examples 14 or 15 to optionally include a cup that can be configured to prevent rotation and pivoting of the rod housing relative to the fastener shaft.

Example 17 can include, or can optionally be combined with the subject matter of one or any combination of Examples 14 through 16 to optionally include a cup that can comprise a high-side and a low-side.

Example 18 can include, or can optionally be combined with the subject matter of one or any combination of Examples 14 through 17 to optionally include a cup that can be configured to prevent pivoting of the rod housing relative to the fastener shaft.

Example 19 can include, or can optionally be combined with the subject matter of one or any combination of Examples 14 through 18 to optionally include a cup that can be circumferentially symmetric.

Example 20 can include, or can optionally be combined with the subject matter of Example 14 to optionally include a first locking component that can comprises a saddle.

Example 21 can include, or can optionally be combined with the subject matter of one or any combination of Examples 14 and 20 to optionally include a saddle that can be configured to prevent pivoting of the rod housing relative to the fastener shaft in a single plane.

Example 22 can include, or can optionally be combined with the subject matter of one or any combination of Examples 14, 20 and 21 to optionally include a saddle that can comprises a pair of high-sides and a pair of low-sides.

Example 23 can include, or can optionally be combined with the subject matter of one or any combination of Examples 14, 20 and 21 to optionally include a saddle that can comprise a high-side, a truncated high-side and a pair of low-sides.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A bone anchor directional component comprising:
    a first body portion having a first outer diameter larger than a shaft diameter of a threaded fastener shaft of a bone anchor;
    a first threaded bore extending through the first body portion, the first threaded bore sized to receive and threadedly engage the threaded fastener shaft of the bone anchor; and
    a first locking component extending from the first body portion and configured to engage an exterior side of a rod housing of the bone anchor to limit movement of the housing relative to the threaded fastener shaft, the first locking component comprising:
    a high side comprising a flat inner surface; and
    a low side comprising a curved inner surface.

2. The bone anchor directional component of claim 1, wherein the first locking component comprises a cup.

3. The bone anchor directional component of claim 2, wherein the cup is configured to prevent rotation and pivoting of the rod housing relative to the fastener shaft.

4. The bone anchor directional component of claim 3, wherein the cup comprises:
    a lower bowl portion;

a high-side extending from the lower bowl portion, the high-side comprising a first radially outer surface and a first radially inner surface configured to engage a first exterior side surface of the rod housing; and a low-side extending from the lower bowl portion, the low-side comprising a second radially outer surface and a second radially inner surface configured to engage a second exterior side surface of the rod housing.

5. The bone anchor directional component of claim 2, wherein the cup is configured to prevent pivoting of the rod housing relative to the fastener shaft.

6. The bone anchor directional component of claim 5, wherein the cup is circumferentially symmetric.

7. The bone anchor directional component of claim 1, wherein the first body portion is configured to be threaded along the threaded fastener shaft to engage a radially outer exterior side of the rod housing to influence a pre-existing coupling between the threaded fastener shaft and the rod housing.

8. A bone anchor system for a poly-axial bone anchor, the bone anchor system comprising:
 a fastener comprising:
  a shaft having a shaft diameter;
  an anchoring projection on the shaft; and
  a head at an end of the shaft;
 a rod housing connected to the head of the fastener, the rod housing comprising:
  a lower housing including a bore through which the shaft extends and against which the head is configured to rotate and pivot in multiple directions; and
  an upper housing connected to the lower housing and including a pair of opposing arms between which a rod can be positioned; and
 a first directional component configured for connection to the fastener, the first directional component comprising:
  a first body portion having a first outer diameter larger than the shaft diameter;
  a first bore extending through the first body portion, the first bore sized to receive the shaft diameter; and
  a first locking component extending from the first body portion configured to engage the rod housing to limit movement of the housing;
 wherein the first locking component comprises a circumferentially symmetric cup configured to prevent rotation and pivoting of the rod housing relative to the fastener.

9. A bone anchor system comprising:
 a fastener comprising:
  a shaft having a shaft diameter;
  an anchoring projection on the shaft; and
  a head at an end of the shaft;
 a rod housing connected to the head of the fastener, the rod housing comprising:
  a flat side;
  a curved side; and
  a bottom side from which the flat side and the curved side extend and from which the fastener projects; and
 a first directional component that is not integrated into the rod housing and that is configured for connection to the fastener, the first directional component comprising:
  a first body portion having a first outer diameter larger than the shaft diameter;
  a first bore extending through the first body portion, the first bore sized to receive the shaft diameter; and
  a first locking component extending from the first body portion configured to engage the rod housing to limit rotating and pivoting of the housing relative to the fastener when the first bore of the first body portion is engaged with the shaft of the fastener, wherein the first locking component comprises a cup comprising:
   a high-side having an inner surface configured to extend along an exterior surface of the flat side;
   a low-side having an inner surface configured to extend along an exterior surface of the curved side; and
   a lower-bowl from which the high-side and the low-side extend and through which the first bore extends, the lower-bowl configured to engage the bottom side.

10. The bone anchor system of claim 9, wherein the cup is circumferentially symmetric.

11. The bone anchor system of claim 9, wherein the first directional component is configured to be disengaged and engaged with the housing axially along a center axis of the shaft of the fastener without separating the housing from the fastener.

* * * * *